US008907061B2

(12) United States Patent
Chromy et al.

(10) Patent No.: US 8,907,061 B2
(45) Date of Patent: Dec. 9, 2014

(54) NANOLIPOPROTEIN PARTICLES AND RELATED METHODS AND SYSTEMS FOR PROTEIN CAPTURE, SOLUBILIZATION, AND/OR PURIFICATION

(75) Inventors: Brett A. Chromy, Danville, CA (US); Paul Henderson, Dublin, CA (US); Paul D. Hoeprich, Jr., Pleasanton, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 1317 days.

(21) Appl. No.: 12/352,548

(22) Filed: Jan. 12, 2009

(65) Prior Publication Data
US 2009/0192299 A1    Jul. 30, 2009

Related U.S. Application Data

(60) Provisional application No. 61/020,638, filed on Jan. 11, 2008, provisional application No. 61/115,446, filed on Nov. 17, 2008.

(51) Int. Cl.
*C07K 14/00* (2006.01)
*C12P 3/00* (2006.01)
*C12N 11/02* (2006.01)

(52) U.S. Cl.
CPC . *C12P 3/00* (2013.01); *C12N 11/02* (2013.01); *Y10S 977/799* (2013.01)
USPC .......................................... 530/350; 977/799

(58) Field of Classification Search
None
See application file for complete search history.

(56) References Cited

U.S. PATENT DOCUMENTS

| | | | | |
|---|---|---|---|---|
| 5,393,530 | A * | 2/1995 | Schneider et al. | 424/450 |
| 7,083,958 | B2 * | 8/2006 | Sligar et al. | 435/183 |
| 2005/0182243 | A1 | 8/2005 | Sligar et al. | |
| 2009/0136937 | A1 | 5/2009 | Coleman et al. | |
| 2011/0059549 | A1 | 3/2011 | Coleman et al. | |
| 2011/0195450 | A1 | 8/2011 | Kudlicki et al. | |

FOREIGN PATENT DOCUMENTS

| | | |
|---|---|---|
| WO | WO 02/40501 | 5/2002 |
| WO | WO 2004/094651 | 11/2004 |
| WO | 2007/053655 | 5/2007 |
| WO | WO 2008/106660 | 9/2008 |

OTHER PUBLICATIONS

Craig D. Blanchette, et al., "Atomic Force Microscopy Differentiates Discrete Size Distributions Between Membrane Protein Containing and Empty Nanolipoprotein Particles" *Biochimica et Biophysica Acta*; vol. 1788, pp. 724-731 (2009; pre-published electronically on Dec. 8, 2008).

Restriction Requirement issued for U.S. Appl. No. 12/118,530, filed May 9, 2008, in the name of Matthew A. Coleman et al.; mail date: Mar. 30, 2011.
Restriction Requirement issued for U.S. Appl. No. 12/352,472, filed Jan. 12, 2009, in the name of Sarah E. Baker et al.; mail date: May 27, 2011.
Restriction Requirement issued for U.S. Appl. No. 12/118,396, filed May 9, 2008, in the name of Matthew A. Coleman et al.; mail date: Mar. 4, 2011.
Dunn, R. J. et al., "Structure-functions studies on bacteriorhodopsin" Expression of the bacterio-opsin gene *Escherichia coli*, vol. 262, No. 19, pp. 9246-9254, Jul. 5, 1986.
Sonar, S et al., "Cell-Free Synthesis, Functional Refolding and Spectroscopic Characterization of Bacteriorhodopsin, an Integral Membrane Protein", Biochemistry, vol. 32, pp. 13777-13781, Oct. 25, 1993.
Kalmbach, R., et al., "Functional Cell-free synthesis of a seven helix membrane protein: In situ Insertion of Bacteriorhodopsin in Liposomes", J. Mol. Biol. vol. 371, pp. 639-648, 2007.
Wang, J., et al., "Comparison of the Dynamics of the primary events of bacteriorhodopsin in Its trimeric and monomeric states", Biophysical Journal, vol. 83, pp. 1557-1566, Sep. 2002.
Bayburt, T. H., et al., "Assembly of single bacteriorhodopsin trimers in bilayer nandiscs", Archives of Biochemistry and Biophysics, pp. 215-222, 2006.
Chromy, B. A., et al., "Different Apolipoproteins Impact Nanolipoprotein Particle Formation", J. Am. Chem. Soc., vol. 129, pp. 14348-14354, Oct. 27, 2007.
Bayburt, T. H., et al., "Reconstitution and Imaging of a Membrane Protein in a Nanometer-Size Phospholipid Bilayer" Journal of Structural Biology, pp. 37-44, 1998.
Forstner, M., et al., "Carboxyl-Terminal domain of Human Apolipoprotein E: Expression, Purification, and Crystallization", Protein Expression and Purification, vol. 17, pp. 267-272, 1999.
Morrow, J. A., et al., "Functional Characterization of Apolipoprotein E Isoforms Overexpressed in *Escherichia coli*", Protein Expression and Purification, vol. 16,pp. 224-230, 1990.
Jayaraman, S., et al., "Structural Basis for Thermal Stability of Human Low-Density Lopoprotein", Biochemistry 44, pp. 3965-3971, 2005.
Gursky, o., et al., Compex of Human Apolipoprotein C-1 with Phospholipid: Thermodynamic or Kinetic Stability? Biochemistry 41, pp. 7373-7384, 2002.
Coleman, M., et al., "Asp 46 can substitute for Asp 96 as the Schiff Base Proton Donor in Bacteriorhodopsin", Biochemistry 34, pp. 15599-15606, 1995.
Klammt, C., et al., "High level cell-free expression and specific labeling of integral membrane proteins", Eur. J. Biochem, 271, pp. 568-580, 2004.

(Continued)

*Primary Examiner* — Anand Desai
(74) *Attorney, Agent, or Firm* — Steinfl & Bruno, LLP

(57) ABSTRACT

Provided herein are methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

6 Claims, 35 Drawing Sheets

(56) References Cited

OTHER PUBLICATIONS

Klammt, C., et al., "Cell-free expression as an emerging technique for the large scale production of integral membrane protein" FEBS Journal, 273, pp. 4141-4153, 2006.
Sonar, S., et al., "A redirected proton pathway in the bacteriorhodopsin Mutan Tyr-57→Asp", The Journal of Biological Chemistry, vol. 269, No. 46, pp. 28851-28858, Nov. 18, 1994.
Klammt, C., et al., "Evaluation of detergents for the soluble expression of α-helical and β-barrel-type integral membrane proteins by a preparative scale individual cell-free expression system", FEBS Journal, pp. 6024-6038, 2005.
Camarero, J. A., et l., "Chemoselective Attachment of Biologically Active Protein to Surfaces by Expressed Protein Ligation and Its Application for Protein Chip' Fabrication", J.A. Chem. Soc., vol. 126, pp. 14730-14731, 2004.
Rao, R.S., et al., "Comparison of Multiplexed techniques for detection of bacterial and Viral Proteins", Journal of Proteome Research, 3, pp. 736-742, 2004.
Segelke, B. W., et al., "Laboratory scale structural genomics", Journal of Structural and Functional Genomics 5, pp. 147-157, 2004.
Lu, B., et al., "Conformational reorganization of the four-helix bundle of human apolipoprotein E in Binding to Phospholipid", The Journal of Biological Chemistry, vol. 275, No. 27, pp. 20775-20781, Jul. 7, 2000.
Wientzek, M., et al., "Binding of Inspect Apolipophorin III to Dimyristoylphosphatidylcholine Vesicles", The Journal of Biological Chemistry, vol. 269, No. 6, pp. 4605-4612, 1994.
Forte T.M., "Electron microscope study on reassembly of plasma high density apoprotein with various lipids", Biochimi. Biophys. Acta, 248, pp. 381-386, 1971.
Abdulreda, M.H, Atomic Force Microscope Spectroscopy Reveals a Hemifusion Intermediate during Soluble $N$-Ethylmaleimide Sensitive Factor-Attachment Protein Receptors-Mediated Membrane Fusio, Biophysical Journal, vol. 94, pp. 648-655, Jan. 2008.
PCT International Search Report for PCT/US2008/063307 filed on Sep. 5, 2008 in the name of Lawrence Livermore National Security, LLC.
PCT Written Opinion for PCT/US2008/063307 filed on Sep. 5, 2008 in the name of Lawrence Livermore National Security, LLC.
Bayburt, T. H., et al., "Self-assembly of single integral membrane proteins into soluble nanoscale phospholipid bilayers", Protein Science vol. 12, No. 11, Nov. 2003, pp. 2476-2481, XP002498218 ISSN: 0961-8368.
North P. and Fleischer S. "Alteration of Synaptic Membrane Cholesterol/Phospholipid Ratio Using a Lipid Transfer Protein", (1983) J. Biol. Chem. vol. 258, No. 2. pp. 1242-1253.
Bockaert J., Brand C., Journot, L. (1997), Do Recombinant Receptor Assays Provide Affinity and Potency. In Receptor Classification: The integration of operational, structural, and transductional information (D.G. Trist, P.P.A. Humphrey, P. Leff, and N.P. Shankley, Eds.). vol. 812. New York, New York Academy of Sciences.
Tufteland M. et al., "Peptide Stabilized Amphotericin B nanodisks", Peptides (2007) 28:741-748.
Jonas, A. "Reconstitution of High-Density Lipoproteins", Methods Enzymol. 1986, 128, 553-82.
Bayburt, T. H.; Grinkova, Y. V.; Sligar, S. G. "Self-Assembly of Discoidal Phospholipid Bilayer Nanoparticles with membrane scaffold proteins", Nano Lett. 2002, 2, 853-856.
J. Wang, S. Link, C.D. Heyes and M.A. El-Sayed, Comparison of the dynamics of the primary events of bacteriorhodopsin in its trimeric and monomeric states, Biophys. J. 83 (2002), pp. 1557-1566.
G. Bacher, R. Korner, A. Atrih, S.J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of peptidoglycan fragments isolated from various bacillus species, J. Mass Spectrom. 36 (2001), pp. 124-139.
Sapra R et al, "Purification and characterization of a Membrane-Bound Hydrogenase from the Hyperthermophilic Archaeon *Pyrococcus furiosus*", J Bacteriol. 2000 182, (12) 3423-3428.
Sapra R et al,. "A simple energy-conserving system: Proton reduction coupled to proton translocation", J Bacteriol 2003, 100 (13), 7545-7550.
Pasini EM et al., In depth analysis of the membrane and cytosolic proteome of red blood cells, 2006 Blood, 108: 791-801.
G. Bacher et al., "Charge-reduced nano electrospray ionization combined with differential mobility analysis of peptides, proteins, glycoproteins, non covalent protein complexes and viruses", Journal of Mass Spectrometry 2001; 36: 1038-1052.
Goldet, G.; Wait, A. F.; Cracknell, J. A,; Vincent, K. A.; Ludwig, M.; Lenz, Friedrich, B.; Armstrong, F. A. , "Hydrogen Production under Aerobic Conditions by Membrane-Bound Hydrogenases from Ralstonia Species", Journal of the American Chemical Society 2008, 130, (33),1, 1106-1113.
Cracknell, J. A.; Vincent, K. A.; Ludwig, M.; Lenz, O.; Friedrich, B.; Armstrong, F. A., "Enzymatic oxidation of H2 in Atmosphere O2", Journal of the American Chemical Society 2007, 130,424-425.
Kovacs, K. L.; Maroti, G.; Rakhely, G., "A novel approach for biohydrogen production", International Journal of Hydrogen Energy 2006, 31, (1 I), 1460-1468.
Ho, D.; Chu, B.; Lee, H.; Brooks, E. K.; Kuo, K.; Montemagno, C. D., "Fabrication of biomolecule-copolymer hybrid nanovesicles as energy conversion systems", Nanotechnology 2005, 16, (12), 3120-3132.
Vincent, K. A.; Cracknell, J. A,; Lenz, O.; Zebger, I.; Friederich, B.; Armstrong, F., "Electrocatalytic hydrogen oxidation by an enyme at high carbon monoxide or oxygen levels", Proceedings of the National Academy of Sciences 2005,102, (47),16951-16954.
Zhang, Y.-H. P.; Evans, B. R.; Mielenz, J. R.; Hopkins, R. C.; Adams, M. W. W. "High-Yield Hydrogen Production from Startch and Water by a Synthetic Enzymatic Pathway", PLoS One 2007, e456, (S), 1-6.
Sanderson, K., "The photon trap", Nature 2008, 452, 400-402.
Woodward, J.; Mattingly, S. M.; Danson, M.; Hough, D.; Ward, N.; Adams, M. "In vitro hydrogen production by glucose dehydrogenase and hydrogenase", Nature Biotechnology 1996, 14,872-874.
Woodward, J.; Orr, M.; Cordray, K.; Greenbaum, E., "Enzymatic production of biohydrogen", Nature 2000, 405, 1014-1015.
Elgren, T. E.; Zadvomy, O. A.; Brecht, E.; Douglas, T.; Zorin, N. A,; Maroney, M. J.; Peters, "Immobilization of Active Hydrogenases by Encapsulation in polymeric porous gels", Nano Letters 2005 vol. 5, No. 10 2085-2087.
Borch, J. et al., "Nanodiscs for immobilization of Lipid Bilayers and Membrane Receptors:", Analytical Chemistry 2008,80, (16), 6245-6252.
Blanchette, C. D.; Law, R.; Benner, W. H.; Pesavento, J. B.; Cappuccio, J. A,; Walsworth, V. L.; Kuhn, E. A,; Corzette, M.; Chromy, B. A,; Segelke, B. W.; Coleman, M. A,; Bench, G.; Hoeprich, P. D.; Sulcheck, T. A. "Quantifying Distributions . . . ", Journal of Lipid Research 2008,49, (7), 1420-1430.
Chromy, B. A.; Arroyo, E.; Blanchette, C. D.; Bench, G.; Benner, H.; Cappuccio, J. A,; Coleman, M. A.; Henderson, P. T.; Hinz, A. K.; Kuhn, E. A.; Pesavento, J. B.; Segclke, B. W.; Sulcheck, T. A.; Tarasow, T.; Walsworth, V. L.; Hoeprich, P. D., "Different Apolipoproteins Impact Nanolipoprotein Particle Formation", Journal Of the American Chemical Society 2007, 129, 14348-14354.
Nath, A,; Atkins, W. M.; Sligar, S. G. "Applications of Phospholipid . . . ", Biochemistry 2007,46, (8), 2059-2069.
Boldog, T.; Grimme, S.; Li, M.; Sligar, S.; Hazelbauer, G. L. "Nanodiscs separate chemoreceptor oligomeric states and reveal their signaling properties," Proceedings of the National Academy of Sciences 2006, 103, (31), I 1509-11514.
Leitz, A. J.; Bayburt, T. H.; Basnakov, A. N.; Springer, B. A,; Sligar, S. G., "Functional reconstitution of B2-adrenergic receptors utilizing self-assembling Nanodisc technology", Biotechniques 2006, 40, (5), 60 1-6 12.
Hedderich, R., "Energy-Converting [NiFi] Hydrogenases From Archaea and Extremophiles", Journal of Bioenergetics and Biomembranes 2004, 36, (1), 65-75.

(56) References Cited

OTHER PUBLICATIONS

Vignais PM. ; Billoud B. Ocurrence, Classification, and Biological Function of Hydrogenases: An overview. Chemical Reviews 2007, 107, 4206-4272.

Jed O. Eberly and Roger L. Ely, "Thermotolerant Hydrogenases", Critical Reviews in Microbiology, 34:117-130, 2008.

Sun, X. et al . Membrane-Mimetic Films of Aymmetric Phosphtidylcholine Lipid Bolaamphiphiles. Langmuir 2006,22, 1201-1208.

Meyer, J. "Fe/Fe hydrogenases and their evolution: a genomic perspective." Cell. Mol. Life. Sci. 64 2007 1063-1084.

Vincent, K. A. et al. "Investigating and Exploiting the Electrocatalytic Properties of Hydrogenases" Chern. Rev. 2007 107, 4366-4413.

Parkin, A., Goldet, G. Cavazza, C. Fontecilla-Camps, J., Armstrong, F. J., "The difference a Se Makes?", Am Chern. Soc. 2008,13 (40) 13410-13416.

Restriction Requirement issued Sep. 24, 2010 for U.S. Appl. No. 12/118,530, filed May 9, 2008 in the name of Matthew A. Coleman et al.

Dunn, R., et al., Structure-function studies on Bacteriorhodospin, The Journal of Biological Chemistry 1987, 262: 9246-9254.

Non-Final Office Action mailed on Sep. 22, 2011 for U.S. Appl. No. 12/352,472, filed Jan. 12, 2009 in the name of Sarah E. Baker et al.

Final Office Action mailed on Jun. 7, 2012 for U.S. Appl. No. 12/352,472, filed Jan. 12, 2009 in the name of Sarah E. Baker et al.

Non-Final Office Action mailed on Aug. 30, 2011 for U.S. Appl. No. 12/118,396, filed May 9, 2008 in the name of Matthew A. Coleman et al.

Non-Final Office Action mailed on Aug. 30, 2011 for U.S. Appl. No. 12/118,530, filed May 9, 2008 in the name of Matthew A. Coleman et al.

Final Office Action mailed on Jan. 25, 2012 for U.S. Appl. No. 12/118,530, filed May 9, 2008 in the name of Matthew A. Coleman et al.

Final Office Action mailed on Jan. 18, 2012 for U.S. Appl. No. 12/118,396 filed on May 9, 2008 in the name of Matthew A. Coleman et al.

Wuu, J.J., et al., High yield cell-free production of integral membrane proteins without refolding or detergents, Biochim. et Biophyica Acta 2008, 1237-1250.

Civjan, N., et al., Direct solubilization of heterologously expressed membrane proteins by incorporation into nanoscale lipid bilayers, BioTechniques 2003, 35: 556-563.

Persson, B., et al., Topology prediction of membrane proteins, Protein Science 1996, 5:363-371.

J.R. Wetterau & A. Jonas, "Effect of Dipalmitoylphosphatidylcholine Vesicle Curvature on the Reaction with Human Apolipoprotein A-I", The Journal of Biological Chemistry, 1982, 257:10961-10966.

J.R. Silvius, "Thermotropic Phase Transitions of Pure Lipids in Model Membranes and Their Modification by Membrane Proteins", 1982, New York: Wiley, Ch. 7, pp. 239-281.

P.R. Cullis, et al., "Physical Properties and Functional Roles of Lipids in Membranes", 1991, New York: Elsevier, vol. 20, Ch. 1, pp. 1-41.

\* cited by examiner

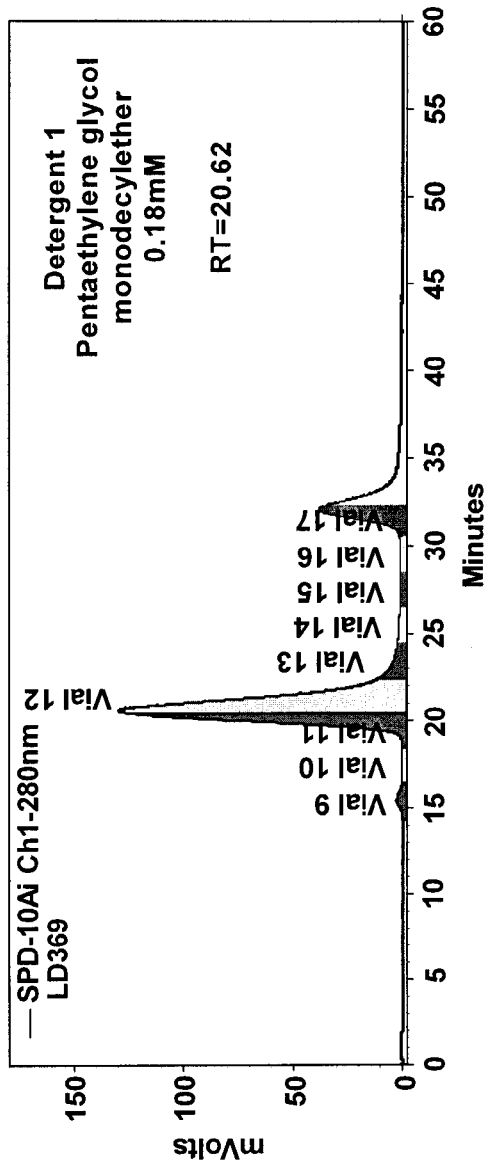
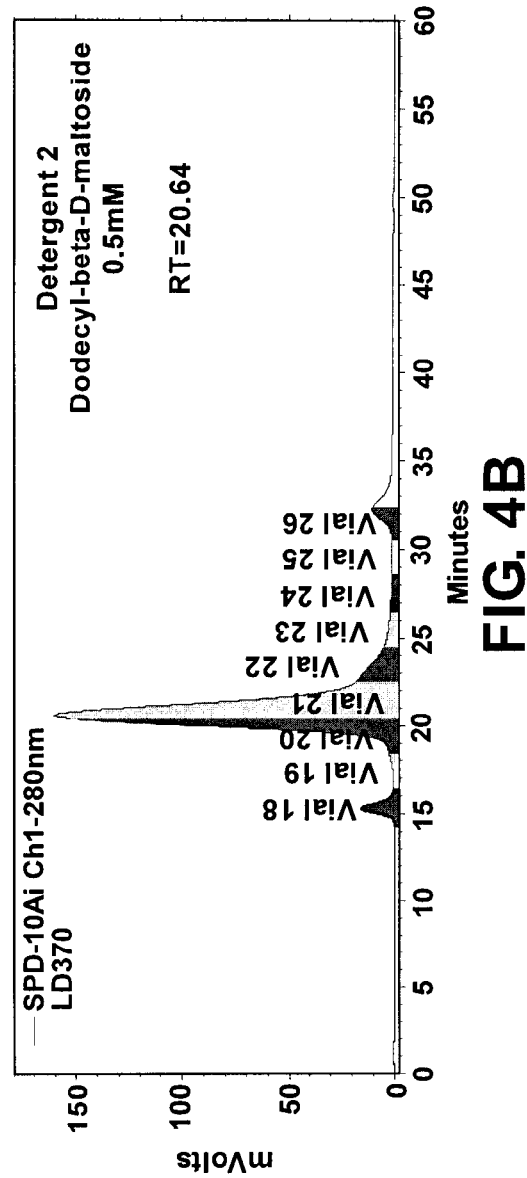
FIG. 4A
FIG. 4B

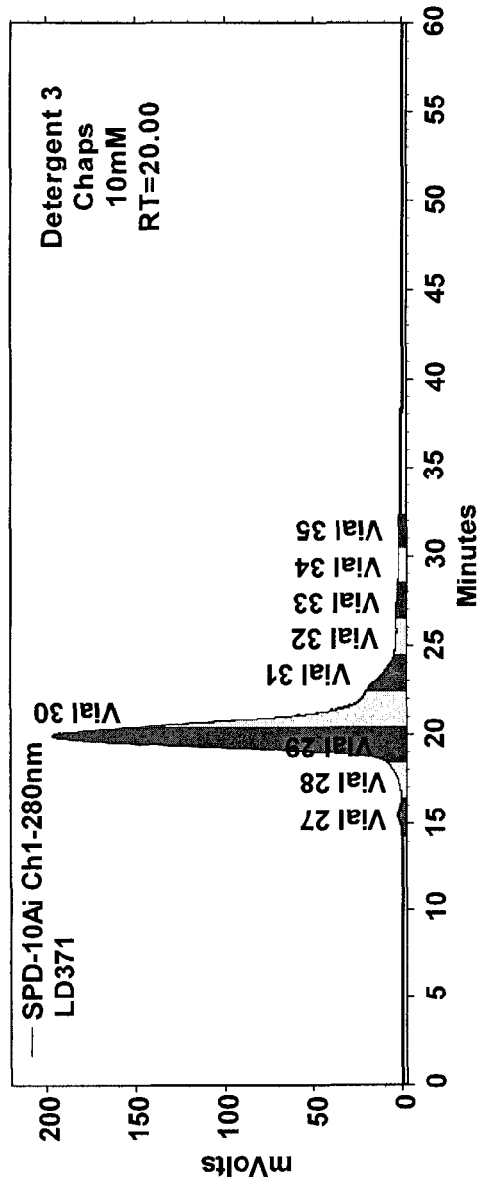
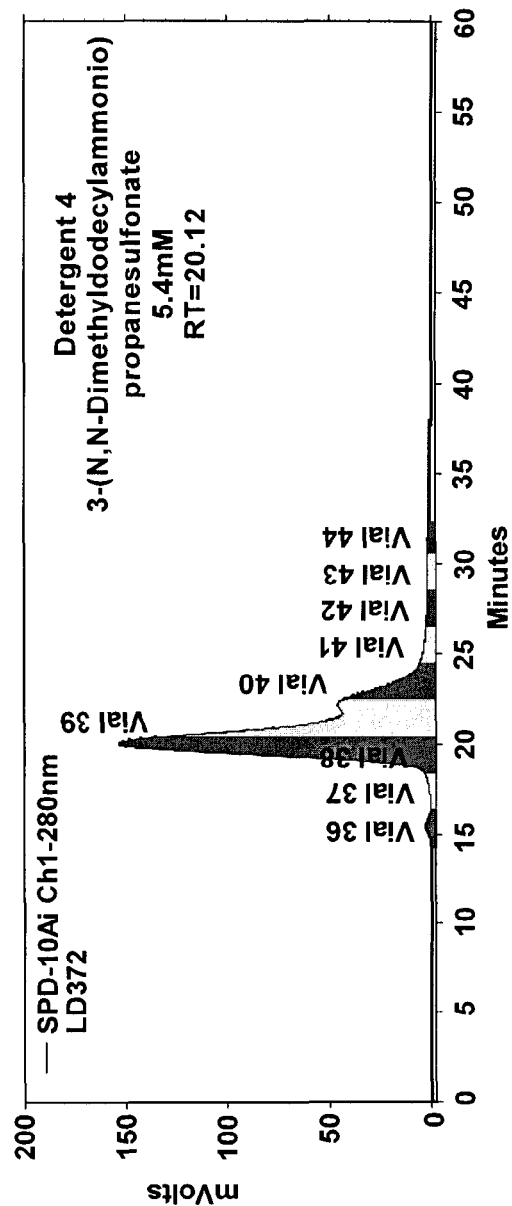

SEC shows successful H-NLPs, smaller than liposomes, larger than empty NLPs

H-NLPs are larger than empty NLPs

| Sample | Mol Wt. | Stokes D |
|---|---|---|
| Empty | 710 kDa | 15.9 |
| 25 ug | 1465 kDa | 21.1 |
| 25 ug | 1500 kDa | 21.3 |
| 10ug | 820 kDa | 16.8 |
| 10ug | 785 kDa | 16.5 |
| No E con | 2240 kDa | 24.9 |

FIG. 18

NANOLIPOPROTEIN PARTICLES AND RELATED METHODS AND SYSTEMS FOR PROTEIN CAPTURE, SOLUBILIZATION, AND/OR PURIFICATION

CROSS REFERENCE TO RELATED APPLICATIONS

This application claims priority to U.S. Provisional Application entitled "Functional membrane protein capture, solubilization, and purification from native cell membrane fractions using nanolipoprotein particles formed in situ" Ser. No. 61/020,638, filed on Jan. 11, 2008 and to U.S. Provisional Application entitled "Hydrogen Production by Membrane Associated Hydrogenases in Soluble Nanolipoprotein Particles" Ser. No. 61/115,446, filed on Nov. 17, 2008 , the disclosure of each of which is incorporated herein by reference in its entirety. This application may also be related to U.S. application entitled "Methods and Systems for Monitoring Production of a Target Protein in a Nanolipoprotein Particle" Ser. No. 12/118,530, filed on May 9, 2008, to U.S. application entitled "Methods and Systems for Producing Nanolipoprotein Particle" Ser. No. 12/118,396, filed on May 9, 2008, and to U.S. application entitled "Nanolipoprotein Particles comprising Functional Membrane Associated Biocatalysts and related Assemblies, Methods and Systems", filed on the same day of the present application, the disclosure of each of which is incorporated herein by reference in its entirety.

STATEMENT OF GOVERNMENT GRANT

The United States Government has rights in this invention pursuant to Contract No. DE-AC52-07NA27344 between the U.S. Department of Energy and Lawrence Livermore National Security, LLC.

FIELD

The present disclosure relates to nanolipoprotein particles (NLPs) and in particular to NLPs and related methods and systems for capturing, solubilizing and/or purifying a target protein, and in particular a membrane associated protein.

BACKGROUND

Membrane-associated proteins and protein complexes account for ~30% or more of the cellular proteins. Membrane proteins are held within a bilayer structure. The basic membrane bilayer construct consists of two opposing layers of amphiphilic molecules know as phospholipids; each molecule has a hydrophilic moiety, i.e., a polar phosphate group/derivative, and a hydrophobic moiety, i.e., a long hydrocarbon chain. These molecules self-assemble in a biological (largely aqueous) environment according to thermodynamics associated with water exclusion or hydrophobic association.

In order to facilitate the myriad functions of biological membranes including the passage of nutrients, signaling molecules and other molecules into and out of the cell, membrane proteins are arrayed in the bilayer structure. In particular, some proteins span the bilayer, others are anchored within the bilayer, and still others organize "peripheral" proteins into complexes. Many membrane bound protein complexes mediate essential cellular processes e.g. signal transduction, transport, recognition, and cell-cell communication.

In general, this class of proteins is challenging to study because of their insolubility and tendency to aggregate when removed from their protein lipid bilayer environment. Generally, although membrane proteins are optimally folded and functional when in a lipid bilayer, certain standard protein purification methods often remove lipids, invariably altering protein conformation and function.

Additionally, certain organisms, such as gram negative bacteria or plants, have membranes (e.g. outer membrane of gram negative bacteria), that are structurally different than the typical bilayer. Furthermore in gram negative bacteria, some membrane associated proteins span the inner membrane and outer membrane of the bacteria. Purification of membrane associated proteins from those organisms can be particularly challenging and many of those proteins often do not maintain their function following extraction.

The above challenges often make derivation and study of membrane proteins and membrane proteomes particularly difficult due to the complex structure and solubility of all the membrane proteins in a particular membrane fraction.

SUMMARY

Provided herein, are methods, which, in several embodiments, allow assembling, solubilizing and/or purifying in a NLP, membrane associated proteins of any size, number and/or type in their functional form to the extent of allowing comprehensive proteomic analysis of several kinds of membranes, including outer membrane of gram negative bacteria and membranes of plant cells.

According to a first aspect, a method for assembling a membrane associated protein with a scaffold protein, and a membrane forming lipid into a nanolipoprotein particle, is described. The membrane forming lipid has a membrane forming lipid gel-crystalline transition temperature, and the method comprises: contacting the membrane associated protein with the scaffold protein and the membrane forming lipid to provide an admixture. The method further comprises subjecting the admixture to a temperature transition cycle in presence of a detergent, for a time and under condition to allow assembly of the nanolipoprotein particle. In the method, the temperature transition cycle comprises: a temperature increase step and a temperature decrease step. In the temperature increase step the admixture is brought to a temperature above the membrane forming lipid gel crystalline transition temperature. In the temperature decrease step the admixture is brought to a temperature below the membrane forming lipid gel crystalline transition temperature.

According to a second aspect, a method for solubilizing a membrane associated protein comprised in a cell membrane is described. The method comprises: contacting the cell membrane with a scaffold protein and a membrane forming lipid to provide an admixture. The method further comprises subjecting the admixture to a temperature transition cycle in presence of a detergent, for a time and under condition to allow assembly of a nanolipoprotein particle comprising a solubilized membrane associated protein. In the method, the membrane forming lipid has a membrane forming lipid gel-crystalline transition temperature; and the temperature transition cycle comprises: a temperature increase step wherein the admixture is brought to a temperature above said membrane forming lipid gel crystalline transition temperature and a temperature decrease step wherein the admixture is brought to a temperature below said membrane forming lipid gel crystalline transition temperature.

According to a third aspect, a method for purifying a membrane associated protein from a cell membrane into a nanolipoprotein particle is disclosed, the method comprises: contacting the cell membrane with a scaffold protein and a membrane forming lipid to provide an admixture, and subjecting the admixture to a temperature transition cycle in presence of a detergent, for a time and under condition to allow assembly of a nanolipoprotein particle comprising the target protein. The method can further comprise isolating the target protein from the nanolipoprotein particle. In the method, the membrane forming lipid has a membrane forming lipid gel-crystalline transition temperature and the temperature transition cycle comprises: a temperature increase step wherein the admixture is brought to a temperature above said membrane forming lipid gel crystalline transition temperature and a temperature decrease step wherein the admixture is brought to a temperature below said membrane forming lipid gel crystalline transition temperature.

The methods herein described can be used, in several embodiments, to assemble, solubilize and/or purify in the NLPs any kind of membrane protein of interest, including integral membrane proteins and other proteins difficult to manipulate with current methods.

The methods herein described can also be used, in several embodiments, to assemble, solubilize and/or purify in the NLPs of any size including complex membrane proteins formed by several subunits.

The methods herein described can further be used, in several embodiments, to assemble, solubilize and/or purify in the NLPs a controlled number of membrane associated proteins to the extent of allowing a proteomic analysis of a membrane or membrane fraction that is more comprehensive and/or performed with a more simplified procedure, if compared to several current methods.

The methods herein described can also be used, in several embodiments, to assemble, solubilize and/or purify in the NLPs, membrane associated proteins from a wide variety of membrane fractions, including crude membrane preparations of inner and outer membranes of gram-negative bacteria, single bilayer membranes of gram-positive bacteria, and plasma membranes of eukaryotic cells, including yeasts cells and plant cells.

The methods herein described can further be used, in several embodiments, to assemble, solubilize and/or purify in the NLPs, membrane associated proteins in their functional form, thus allowing, harvest, reproduction and/or further analysis of the proteins' structure and activity, as well as the interaction with other proteins.

The methods herein described allow, in several embodiments isolation and harvest of non-recombinantly derived membrane proteins from a variety of cell types, including their native membrane environment.

The methods and systems herein described can be also used in connection with protein purification, membrane protein structure/function, countermeasure discovery, therapeutic discovery, vaccine development, detection of agents that are detrimental to normal cellular function.

In particular, methods and systems herein disclosed can be used, in several embodiments, for performing the purification of membrane proteins simply and easily. Protein purification, membrane protein structure/function, proteomic analysis, countermeasure discovery, therapeutic discovery, vaccine development, and detection of pathogens or poisons can all be enhanced using the methods described herein.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 3A shows an NLP assembly that gives rise to a single SEC peak that corresponds to a homogeneous preparation of NLPs for the purpose of incorporating a large membrane protein or a significant number of membrane proteins. FIG. 3B shows an NLP assembly that results in multiple SEC peaks, usually three when cholate is used as the detergent, that are of different molecular weight and are able to contain more specific amounts and particular membrane proteins of interest.

FIGS. 4A-4F show SEC traces and native gel characterization of empty NLPs made with different detergents. SEC traces of empty NLPs made using five different detergents are shown (FIGS. 4A-4E) with their corresponding native page characterization (FIG. 4F). Although a large number of potential detergents can be used for MP-NLPs, the data here show that these five particular detergents can successfully enable formation of NLPs.

FIG. 18 shows the SEC size characterization of empty NLP and MP-NLPs with different amounts of hydrogenase membrane proteins (25 µg or 10 µg). The "No E control" samples show the insoluble molecular weight of the crude membrane fraction containing the hydrogenase membrane proteins.

DETAILED DESCRIPTION

Figure 1A:
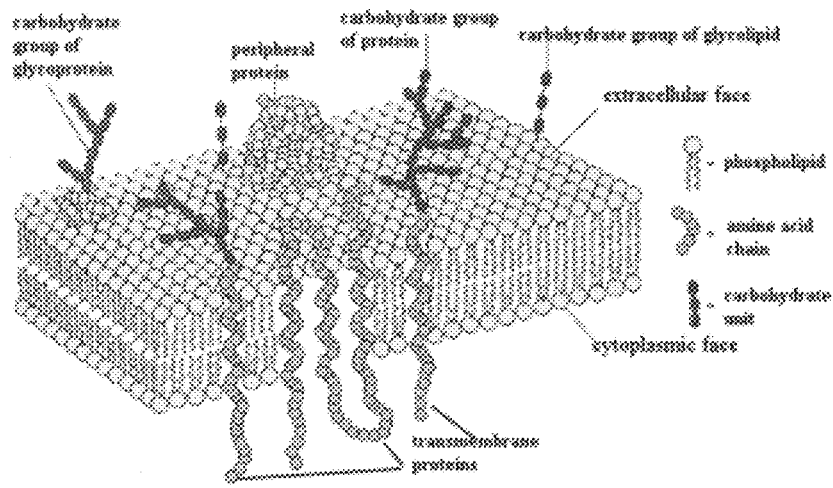
FIG. 1 shows a schematic representation of methods and systems herein disclosed according to some embodiments herein disclosed and where appropriate, referred to as in situ formation.
Figure 1A:
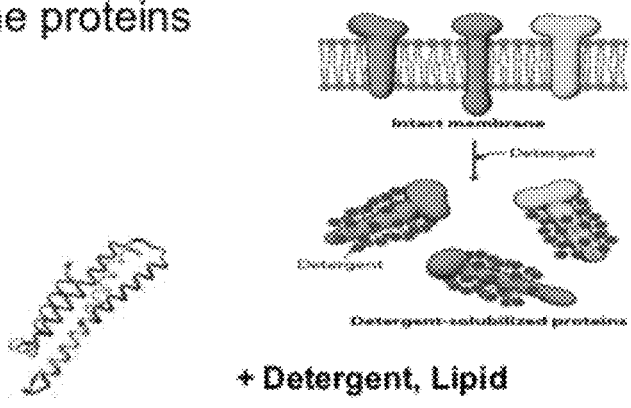
Figure 1A:
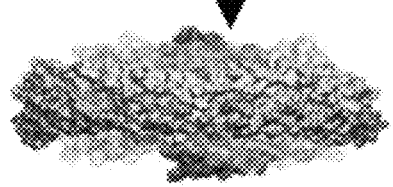

Methods and systems for assembling, solubilizing and/or purifying a membrane associated protein in a NLP particle are provided herein.

The term "assemble" or "assembly" as used herein indicate the fitting together of the components of a molecular structure into said structure. Accordingly, when used with reference to nanolipoproteins, the term "assemble" indicates the fitting together nanolipoprotein components into a nanolipoprotein particle.

The term "solubilize" as used herein indicates to make susceptible or more susceptible to dissolve in a medium and in particular in an aqueous medium. Accordingly, when used with reference to a membrane associated protein the term solubilize indicates making the membrane associated protein soluble or more soluble (susceptible of being dissolved) into a an aqueous environment and encompasses solubilizing proteins from a pellet, a solution, a membrane fraction and any other medium and/or preparations wherein the membrane associated protein is comprised alone or in combination with other compounds and/or molecules.

The term "purify" as used herein indicate the process of freeing something from something. In particular with reference to a membrane associated protein, the term "purify" indicates the act of separating the membrane associated protein from a medium wherein the protein is comprised together with other molecules, and encompasses purification of membrane associated proteins from molecular and/or biological structures such as membranes or molecular complexes. Accordingly, "purifying" a membrane associated protein into a nanolipoprotein particle indicates the act of separating the membrane associated protein from an original environment into the nanolipoprotein particle.

The term "nanolipoprotein particle" "nanodisc" "rHDL" or "NLP" as used herein indicates a supramolecular complex formed by a membrane forming lipid and a scaffold protein, that following assembly in presence of a target protein also include the target protein. The scaffold protein and target protein constitute protein components of the NLP. The membrane forming lipid constitutes a lipid component of the NLP.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide.

As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "scaffold protein" as used herein indicates any protein that is capable of self assembly with an amphipatic lipid in an aqueous environment, organizing the amphipatic lipid into a bilayer, and include but are not limited to apolipoproteins, lipophorines, derivatives thereof (such as truncated and tandemly arrayed sequences) and fragments thereof (e.g. peptides), such as apolipoprotein E4, 22K fragment, liphorin III, apolipoprotein A-1 and the like. In particular, in some embodiments rationally designed amphipathic peptides can serve as a protein component of the NLP.

In some embodiments, the peptides are amphipatic helical peptides that mimic the alpha helices of an apolipoprotein component that are oriented with the long axis perpendicular to the fatty acyl chains of the amphipatic lipid and in particular of the phospholipid.

The wording "membrane associated protein" or "target protein" as used herein indicates any protein having a structure that is suitable for attachment to or association with a biological membrane or biomembrane (i.e. an enclosing or separating amphipathic layer that acts as a barrier within or around a cell). In particular, target proteins include proteins that contain large regions or structural domains that are hydrophobic (the regions that are embedded in or bound to the membrane); those proteins can be extremely difficult to work with in aqueous systems, since when removed from their normal lipid bilayer environment those proteins tend to aggregate and become insoluble. Accordingly, target proteins are protein that typically can assume an active form wherein the target protein exhibits one or more functions or activities, and an inactive form wherein the target protein doe not exhibit those functions/activities. Exemplary target proteins include but are not limited to membrane proteins, i.e. proteins that can be attached to, or associated with the membrane of a cell or an organelle, such as integral membrane proteins (i.e. proteins (or assembly of proteins) that are permanently attached to the biological membrane.), or peripheral membrane proteins (i.e. proteins that adhere only temporarily to the biological membrane with which they are associated). Integral membrane proteins can be separated from the biological membranes only using detergents, nonpolar solvents, or sometimes denaturing agents. Peripheral membrane proteins are proteins that attach to integral membrane proteins, or penetrate the peripheral regions of the lipid bilayer with an attachment that is reversible.

The term "membrane forming lipid" or "amphipatic lipid" as used herein indicates a lipid possessing both hydrophilic and hydrophobic properties that in an aqueous environment assemble in a lipid bilayer structure that consists of two opposing layers of amphipathic molecules known as polar lipids. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols and alkylphosphocholins. Amphipatic lipids include but are not limited to membrane lipids, i.e. amphipatic lipids that are constituents of a biological membrane, such as phospholipids like dimyrisoylphosphatidylcholine (DMPC) or Dioleoylphosphoethanolamine (DOPE) or dioleoylphosphatidylcholine (DOPC). The membrane forming lipid can assume different states in an aqueous environment, including a frozen gel state (here also gel state) and a fluid liquid-crystalline state (here also crystalline state) (Silvius J R 1982), wherein each state is associated with one or more temperatures at which the particular structural phase is detectable (Cullis P R 1991). Therefore each membrane forming lipid has a gel temperature that comprises all the temperatures at which the gel state can be detected and a crystalline temperature that comprises all the temperatures at which the crystalline state can be detected. Additionally, since a membrane forming lipid can transition from a state to another on the basis of the temperature each membrane forming lipid has also a gel-crystalline transition temperature ($T_c$) which is the temperature at which this transition occurs. State temperatures and transition temperatures of various membrane forming lipids can be found by monitoring modifications of the state of the lipid while modifying the temperature of the lipid. Techniques to monitor transitions of states of a lipid are identifiable by a skilled person and include, but are not limited to, dual polarization interferometry (DPI), nuclear magnetic resonance (NMR), Electron Spin Resonance (ESR), fluorescence and differential scanning calorimetry (DSC).

The term "detect" or "detection" as used herein indicates the determination of the existence, presence or fact of an molecule, such as a membrane forming lipid or a target protein and/or related activities in a limited portion of space, including but not limited to a sample, a reaction mixture, a molecular complex and a substrate. A detection is "quantitative" when it refers, relates to, or involves the measurement of quantity or amount of the a membrane forming lipid or a target protein and/or related activities (also referred as quantitation), which includes but is not limited to any analysis designed to determine the amounts or proportions of a membrane forming lipid or a target protein and/or related activities. A detection is "qualitative" when it refers, relates to, or involves identification of a quality or kind of the a membrane forming lipid or a target protein and/or related activities in terms of relative abundance to another a membrane forming lipid or a target protein and/or related activities, which is not quantified.

The membrane forming lipid and the protein components of the NLP are generally able to self-assemble in a biological (largely aqueous) environment according to the thermodynamics associated with water exclusion (increasing entropy) during hydrophobic association.

In the methods and systems herein provided, the amphipatic lipid and the protein components of the NLP are initially contacted to form an admixture. The term "admixture" or "mixture' as used herein indicates a product of mixing the above mentioned components, which in particular can be performed by adding those components in the mixture.

Figure 1B:
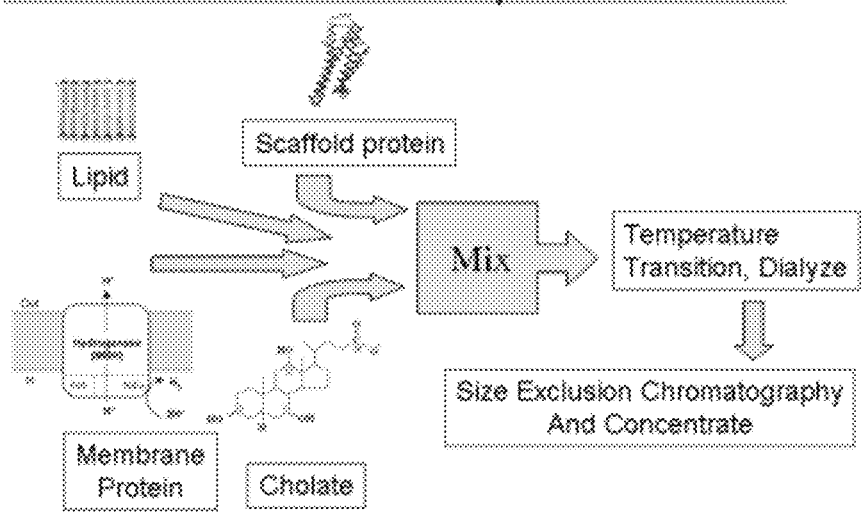
Figure 2:
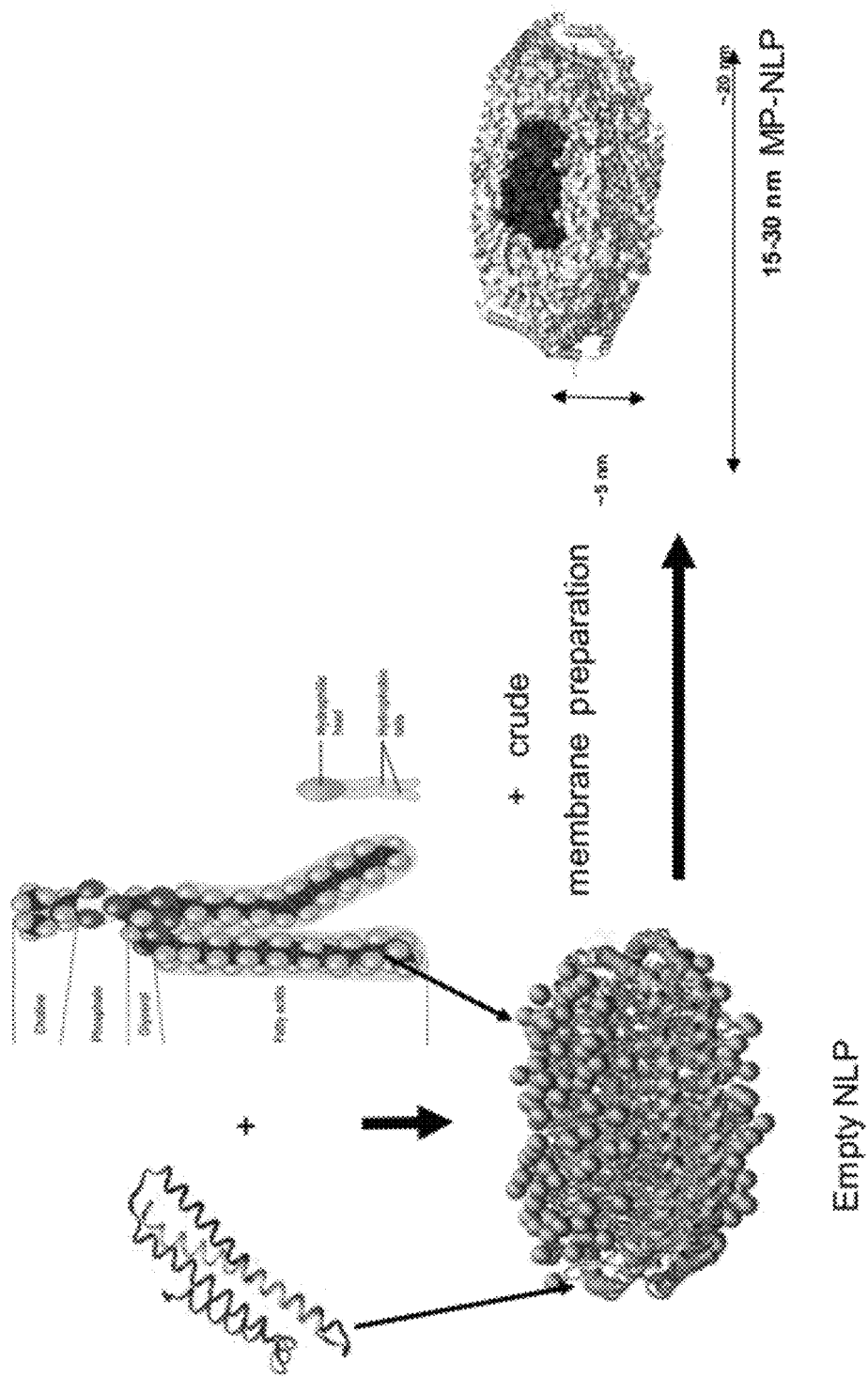
FIG. 2 shows a schematic representation of methods and systems herein disclosed according to an embodiment herein disclosed, and where appropriate, referred to as ex situ formation or intercalation.

In particular, contacting the membrane associated protein with the scaffold protein and the membrane forming lipid can be performed according to the approaches schematically illustrated in FIGS. 1A, 1B and 2. In particular, according to the approaches of FIG. 1A and FIG. 1B the membrane associated protein are contacted with the other NLP components in the mixture to form an NLP including the membrane associated protein. In particular, in the approach of FIG. 1B, the membrane associated protein is pretreated to form a protein/detergent complex that is then contacted with the other NLPs components. The approaches of FIG. 1A or 1B is also indicated as in situ formation of NLPs or in situ approach. In some embodiments, of the in situ approaches the membrane forming lipid can be pre-treated with sonication or detergent solubilization to enable the membrane forming lipid to be soluble and improve the interaction of the lipids and the proteins in the admixture. In the approaches illustrated in FIG. 2, instead the NLP is first formed by any method identifiable by a skilled person or is provided pre-formed, and then contacted with the membrane associated protein using the methods described herein, referred to as ex situ formation or intercalation.

In all the approaches the target protein can be provided in various forms including but not limited to target proteins in a solubilized form (e.g. from a membrane), target proteins comprised in a cell membrane, target proteins comprised in a membrane preparation, and target proteins in other forms identifiable by a skilled person upon reading of the present disclosure.

In particular, in embodiments where solubilization and/or purification of the target protein is desired the target protein can be provided in membranes or membrane preparations, including but not limited to cell membranes and crude membrane extracts. In particular, in embodiments wherein analysis of a target protein from an existing membrane environment is desired, the processing of the membrane environment should be minimized up to contacting the target protein present in a living cell.

In particular, in some embodiments, providing the target protein is performed by providing said protein in a crude cell pellets or membrane fraction. These crude preparations can be obtained through a variety of methods. Such methods can include simple cell lysis and centrifugation or more elaborate techniques that involve density gradients or multiple steps of fractionation.

The wording "crude cell pellets" as used herein indicates samples that contain cellular material that has been lysed through a variety of techniques and then separated from soluble material using centrifugation.

The wording "membrane fraction" as used herein indicates material obtained from crude cell pellets that contain both membrane proteins and membrane lipids, separated from soluble protein and other cellular components.

In some embodiments, the membrane fractions are crude membrane fractions outer or inner membrane fractions from gram-negative bacteria such as *Y. pestis* outer and inner membrane fractions as exemplified in Examples 1 to 6.

In some embodiments, the membrane forming lipid can be contacted with the membrane associated protein and the scaffold protein at a temperature above the membrane forming lipid gel-crystalline transition temperature In the methods herein described the NLP components are contacted in proportions that are functional to the number and/or size of the membrane associated protein to be included in the NLP and are identifiable by a skilled person upon reading of the present disclosure. The appropriate membrane associated protein:lipid ratio is functional to the formation of nanometer-sized, discoidal, particles containing a thermal stable outer scaffold of protein and an inner bilayer membrane mimetic made of lipid molecules that can appropriately accommodate membrane proteins in their midst and can be identified by several methods including protein assays and phospholipid content assays (for example see North P. and Fleischer S. 1983), immunogold cryo-electron microscopy, or STEM-PIXE could all be used to determine the protein lipid ratio. Additionally, the appropriate membrane associated protein:lipid ratio is functional to a complex that does not cause non-functional aggregation of either protein scaffold or membrane protein and one that enables the specific interaction of these components within the entity known as a nanolipoprotein particle, the size and number of the protein to be assembled and usually range from about 6:1 in term of mass for large and/or numerous target proteins and in particular multiple target proteins in a single fraction to about 4:1 for NLPs including multiple target proteins in multiple fractions to even lower ratio for NLP including target protein of small dimensions in single or multiple fractions. Additional ratios among the NLP components that are functional to the desired NLP to be assembled are identifiable by the skilled person and will not be further discussed in details.

Additional components of the admixture are identifiable by a skilled person upon reading of the present disclosure.

In the methods and systems herein provided, once the admixture is formed the amphipatic lipid and the protein components of the NLP are allowed to assemble for a time and under conditions that include subjecting the admixture to a temperature transition cycle in presence of a detergent.

The wording "temperature transition cycle" as used herein indicates a sequence of a temperature increase step and temperature decrease step, wherein the cycle comprises at least one temperature increase step and at least one temperature decrease step. In the temperature transition cycle of the methods herein disclosed, the temperature increase step can precede or follow the temperature decrease step.

In particular, in the temperature increase step of the cycle the admixture is brought to a temperature above the gel-crystalline transition temperature of the membrane forming lipid present in the admixture and selected as a component of the nanolipoprotein particle to be formed. In particular, in the temperature increase step the admixture can be brought to any of the crystalline temperatures of the membrane forming lipid (i.e. any temperature at which the lipid is detectable in a crystalline state). On the other hand, in the temperature decrease step of the cycle, the admixture is brought to a temperature below the gel-crystalline transition temperature of the membrane forming lipid present in the admixture and selected as a component of the nanolipoprotein particle to be formed. In particular, the temperature decrease step, the admixture can be brought to any of the gel temperatures of the membrane forming lipid (i.e. any temperature at which the lipid is detectable in a gel state).

The difference in temperature of the temperature increase step can be the same or different than the difference in temperature of the temperature decrease step and in several embodiments is from about a 24° C. difference in temperature to about 30° difference in temperature.

In the temperature cycle the duration of each step is usually such that at least a fraction, and preferably the majority, of the membrane forming lipid molecules in the mixture change its state. For example, in some embodiments, each step could be performed for about 10 min.

In the methods herein disclosed the admixture has to be subjected to at least one temperature transition cycle. In several embodiments, wherein maximization of the formation of nanolipoprotein particles is desired, the number of temperature transition cycle is increased and the admixture is preferably subjected to multiple transition cycles, which in some embodiments include at least three temperature cycles, in other embodiments include multiple temperature transition cycles performed on the admixture overnight or even a higher number.

In several embodiments, the admixture can be mixed before subjecting the admixture to the temperature transition cycle. In several embodiments the admixture can also be heated to a crystalline temperature, before subjecting the admixture to the temperature transition cycle. This type of lipid pre-treatment may enhance MP-NLP assembly by correcting improperly phased lipid or by eliminating lipid that will not properly associate due to stability, and can be replaced by additional lipid molecules to maintain an appropriate mass ratio An exemplary procedure to perform the temperature transition cycle includes placing the protein-lipid-detergent mixture into a temperature regulated water bath that is below or above the transition temperature of the bulk lipid followed by a water bath that is the opposite of the first water bath relative to the transition temperature. Additional exemplary procedures are illustrated in the examples.

In the methods, the temperature transition cycle is performed in presence of a detergent. The term "detergent" as used herein indicates a surfactant i.e. a wetting agent that lower the surface tension of a liquid, and in particular water, allowing easier spreading, and lower the interfacial tension between two liquids. Detergents include but are not limited to any substance improving fluidity of the membrane forming lipid and solubilization of the membrane associated protein such as cholate or other ionic or non-ionic surfactants.

The wording "in presence" as used herein with reference to the detergent indicates the fact or condition of that detergent of being present in that admixture, which includes but is not limited to presence following addition to the mixture performed In several embodiments, the temperature transition cycle is followed by an incubation step which is performed by bringing the admixture at the temperature transition of the membrane lipid of choice for a predetermined amount of time that is functional to a desired amount of assembled nanolipoprotein particles. For example, in embodiments, wherein the amount of assembled nanolipoprotein particle is maximized the incubation time is also increased. In some embodiments, the incubation step can be performed on the admixture for about 20-24 hr.

In several embodiments, the detergent is removed from the mixture following the temperature transition cycle and the optional incubation. This step is in particular desirable in embodiments wherein stability and/or a reduced variability of the formed NLPs is desired. Removal of the detergent can be performed according to methods that are identifiable by a skilled person and which include dialysis of the detergent from the mixture filtration, dialysis, or other techniques to remove excess detergent, such as bio-beads.

In several embodiments the average yields of the method is between 50 and 70%. The yield was determined by protein assay (Bradford) for the specified membrane protein relative to the empty NLP formulation.

In several embodiments, the admixture is formed due to the gel-liquid-crystalline phase transition of the membrane forming lipid to enhance the contact between the target protein, the membrane forming lipids and the scaffold protein. The admixture is then subjected to a temperature transition cycle in presence of a detergent, for a time and under condition to allow assembly of the nanolipoprotein particle. In the method, the temperature transition cycle comprises: a temperature increase step and a temperature decrease step. In the temperature increase step the admixture is brought to a temperature above the transition temperature forming a fluid liquid-crystalline phase enabling the membrane protein and scaffold protein to better contact the membrane forming lipid. In the temperature decrease step the admixture is brought to a temperature below the membrane forming lipid gel crystalline transition temperature, to help maintain the structure of the assembled species.

The NLP herein disclosed can be formed by lipid bilayers surrounding the membrane protein or proteins from the crude membranes and an apolipoprotein creating a water soluble structure surrounding the lipid bilayer. In some embodiments, the NLP assembled with the method herein described can include multiple target proteins and/or membrane protein complexes.

In some embodiments, the methods herein described are used to incorporate a target protein in a NLP The term "incorporate" or "capture" as used herein indicate the fact, act or condition of a molecule, in particular a membrane associated protein, that is originally comprised in a membrane environment and that following the methods herein described form part an NLP construct.

In some embodiments, the methods and systems herein disclosed can be used to capture and solubilize proteins and protein complexes directly from cell membrane preparations derived from fractionation.

In particular, in several embodiments the methods herein described can be performed from native membrane environments using nanolipoprotein particles formed in situ. These native membrane environments include cell membrane fractions including crude membrane preparations of bacteria and eukaryotic cells. The crude preparations can include the inner and outer membranes of gram-negative bacteria, single bilayer membranes of gram-positive bacteria, and plasma membranes of eukaryotic cells. The preparations can be prepared in many ways, including simple lysis and centrifugation or more elaborate separation schemes that sub-divide the membrane proteins.

In some embodiments, the methods and systems herein disclosed allow direct solubilization of native membrane proteins from both prokaryotic and eukaryotic membrane fractions by in situ NLP formation. NLP formation is accomplished by adding to a cell membrane fraction, purified apolipoprotein, phospholipid and/or a detergent/surfactant. Such NLP constructs will be useful for functional characterization of membrane proteins and membrane protein complexes. Specific membrane lipids including those from fractionated native membranes as extracted from Gram-negative and/or Gram-positive microorganisms, from plant cells, and from eukaryotic cell membranes as well as purified commercially available lipid molecules that constitute membrane forming lipids.

The methods and systems herein described further allow in several embodiments to capture solubilize and/or purify membrane protein in their functional form, thus allowing reproduction and/or further analysis of membrane proteins' activity, including membrane's protein catalytic activity. In some embodiments, the methods and systems herein disclosed allow taking a semi-purified or crude cell membrane fraction derived from classical cell homogenization/fractionation processes and selectively isolating constituent proteins of interest with retention of function. In some embodiments, the methods and systems herein disclosed provide robust nanolipoprotein particle preparation and characterization methods as a platform for physical and/or biochemical characterization of membrane proteins using nanolipoprotein particles.

Functionality of the target protein assembled in the NLP can be detected using techniques identifiable by a skilled person, such as binding experiments for receptor proteins or specific functional assays as described in the literature. Bockaert J. et al., 1997). For example, hydrogenase-containing NLPs can be tested for hydrogen production using GC/MS (as exemplified in the examples and related figures)

In some embodiments, the methods and systems herein disclosed allow incorporation of diverse membrane proteins into NLP constructs, which include but are not limited to integral membrane proteins containing transmembrane a-helices and/or 13-sheet structures, as well as, peripheral and monotopic membrane proteins, Type I, II and III cell-surface receptors and the likes. Membrane proteins that have single or multiple membrane spans can be functionally solubilized into NLPs.

In some embodiments, the methods and systems of the present disclosure enable the quick and easy purification and solubilization of functional membrane proteins from a cell membrane fractions or preparations in a single step.

Suitable applications for NLPs include various biological fields wherein detection of microorganisms and/or analysis of the microorganism is desired since host interactions are mediated through cell surface membrane proteins and are critical to detection, pathogenicity and determination of countermeasure with reference to the microorganism at issue. In particular, nanolipoprotein particles (NLPs) may serve as carriers of non-infective immunogenic proteins, e.g. H5 or N1 proteins (Avian influenza), as potential vaccine-based countermeasures. NLPs can serve as vehicles for delivery of therapeutic-based countermeasures, (Tufteland M Peptides (2007) 28:741-748 Peptides (2007) 28:741-748). Nanolipoprotein particles (NLPs) containing selected microbial (bacterial or viral) cell-surface membrane proteins will provide an opportunity to better understand the science of pathogenicity, e.g. Yop B, D, LcrV, Aile, etc. Nanolipoprotein particles (NLPs) will enable capture and presentation of cell surface protein features associated with known biothreat organisms and potentially could aid in detection of emerging biothreats.

The methods herein described can be used in several embodiments to analyze the total extent of the membrane proteins in a membrane sample, and in particular the proteome of a predetermined membrane fraction more easily and more completely than current methods. In some of those embodiments, forming the admixture and subjecting the admixture to the temperature transition cycle is performed for a time and under conditions that allow capturing the membrane proteome in the NLPs. The NLPs so obtained are then subjected to fractionation (e.g. by electrophoresis on a bidimensional gel) and analysis. A skilled person will be able to identify additional details concerning techniques suitable for analyzing membrane proteomes captured in NLPs according with methods herein described.

The methods herein described can be used in several embodiments to analyze protein-protein interactions. In some of those embodiments, a target protein of interest is capture on an NLP and contacted with one or more candidate proteins under appropriate conditions. Occurrence of interactions can then be detected with techniques identifiable by a skilled person. Various approaches and techniques to analyze the interactions between a membrane associated protein captured in a NLP according to the methods herein disclosed and one or more candidate proteins can be identified by a skilled person and will not be further described in details.

Further details concerning the methods and systems herein disclosed, can be identified by the person skilled in the art upon reading of the present disclosure.

EXAMPLES

The methods and system herein disclosed are further illustrated in the following examples, which are provided by way of illustration and are not intended to be limiting.

In particular, in the following examples, membrane protein incorporation into nanolipoprotein particles (NLPs) is exemplified with reference to membrane proteins from a variety of sources using a variety of methods for crude membrane preparations. Applicants have incorporated outer and inner membrane proteins from bacteria (*Y pestis* and *Acinetobacter Baumannii* respectively) membrane proteins from human red blood cells (RBC membrane) and thermococci (*P. Furiosus*). The majority of the NLP assemblies used crude membrane preparations with lipoprotein E4 N-terminal 22k fragment scaffold and DMPC lipid in the presence of cholate.

The following materials and methods were used to perform the experiments illustrated in the examples Phospholipid 1,2-Dimyristoyl-sn-Glycero-3-Phosphocholine (DMPC): DPMC was purchased from Avanti Polar Lipids, Inc. (Alabaster, Ala.). Although this lipid was the only one used for incorporation in these examples, other lipids, namely POPC, etc. can also be used. Fluorescent lipids have also been used for bR (1% DMPE (NBD-DMPE and RhoB-DMPE) and 10% DMPE and 1% NBD-DMPC).

apoE422k protein production: The expression clone to produce apoE422k, the N-terminal 22 kDa fragment of apolipoprotein E4 (apoE4), as a 6His and thyrodoxin tagged construct was kindly provided by Dr. Karl Weisgraber. Production and purification of apoE422k has been described in detail elsewhere [(Chromy B et al., 2007]. Although this protein was the only one used for scaffold in these examples, other proteins can be used. such as apoA, lipophorins, and other amphipathic lipid-binding proteins.

Membrane fractionation (outer and inner membrane preparations from gram-negative bacteria: The gram-negative bacteria strain is grown from glycerol stocks on blood agar plates with appropriate antibiotics. (e.g., Yp 1283=50 ug/ml Streptomycin). Incubate at 26° c. for ±48 hrs. A swath of colonies is then inoculated in 25 ml of BHI/Str broth (125 ml flask) and the resulting inoculated broth is grown overnight in a water bath at 26° c. with shaking at 225 RPM. Membrane preparations that are different in amount will cause different levels of captured membrane proteins.

The overnight culture is split evenly into 2 small Oakridge tubes and the tubes are spun at 10 K RPM for 10 min at 4° c. The supernatant is discarded and the pellet is frozen at −20° c. or −80° c. The cells are lysed and each (12.5 ml culture) frozen pellet re-suspended in 1.5 ml of B-PER II solution in the hood. Vortex until suspended (usually about 1 minute). 2-10 ul of DNaseI are added per each ml of extract. The resulting mixture is gently mixed in a water bath at 37 c for 20-30 min. (Look for reduced viscosity before proceeding).

Each suspension is then transferred to a 2 ml tube, the tube is spun for 10 min at 10K RPM at 15° c. to remove unlysed cells and the supernatant was decanted into a new tube. From this point on the samples are kept ice-cold.

The suspension is aliquoted evenly into larger ultra tubes (TLA 100.3 rotor), brought up to 3.2 ml with cold *Buffer A, and mixed by pipeting. The samples are then spun in ultracentrifuge at 50K RPM (TLA 100.3 rotor) for 1 hr at 4° c., the supernatant discarded and 2 ml of [Buffer A+2% TRITON] are added to the pellet. The pellet is resuspended by pipeting to break up the pellet and the suspension is incubated on ice for 30 minutes. The ultracentrifugation is repeated for 1 hr at 50K RPM at 4° c., the supernatant (inner membrane) is saved. The pellet is then washed to remove residual triton, the pellet orientation is marked and 1 ml of Buffer A added (pipeting around side-walls when adding buffer).

The solution is spun in ultracentrifuge for 5 min at 50K RPM (place tubes with same orientation as existing pellets), the supernatant discarded and wash and centrifugation are repeated to get rid of all residual triton. The pellet (outer membrane) is resuspended in 500 µl of Buffer A or TBS. Quantitative analysis with SDS gel is ten performed.

A viability test is then performed by plating onto blood agar; growing for 48 hr and if there is growth, filtering through 0.45 or 0.22 µm filter to sterilize and then store in −80° c. Nanodrop 280 absorbance analysis is also performed. Percentage target protein in the sample is estimated from SDS gel and the relevant value adjusted to that value for assembly Nanolipoprotein particle (NLP) formation: MP-NLPs were assembled through a process adapted from the detergent dialysis technique [Jonas, A, et al., 1986]. The final concentration of detergent needs to be maintained above its critical micellar concentration during assembly (Bayburt Nanoletters 2002). Sodium cholate (20 mM) was prepared from a 500 mM stock solution and added to DMPC suspended in Tris buffered saline to a concentration of 34 mg/mL and probe sonicated to clarity. The solution is briefly centrifuged to remove any metal contamination from the probe. For other detergents, see FIGS. 4A-4F. Constituents are combined in the following concentrations; DMPC, 11 mM:apoE422k, 90.9 µM:bR, 49.8 µM; creating a molar ratio of 130:1:1.83 respectively, i.e. lipid (6.52 mM):scaffold protein (44 µM): membrane protein (9.6 µM):detergent (13 mM), creating a ratio of 148:1:0.2:296). The order in which constituents are combined is not necessary to maintain. However, two main techniques exist for assembling MP-NLPs shown in FIG. 1 (in situ) and FIG. 2 (intercalation). "Empty" NLPs (without membrane proteins) were assembled as described by [Chromy B., et al 2007].

NLP assembly formation started with 3 repeated sets of transition temperature incubations, where the temperature was cycled from 30° C. for 10 minutes to 20° C. for 10 minutes, with light hand mixing between incubations. Next, the reaction was incubated overnight at 23.8° C. Cholate was removed by dialysis against 1000× volume of TBS buffer with 3 changes in 24 hrs. The NLPs were purified from lipid-poor and lipid-rich complexes by size-exclusion chromatography (VP HPLC, Shimadzu) using a Superdex 200 HR 10/30 column (GE Healthcare), in TBS at a flow rate of 0.5 ml/min. The column was calibrated with four protein standards of known molecular weight and Stokes diameter that span the separation range of the column and the NLP samples. The void volume was established with Blue dextran. Fractions containing MP-NLPs were concentrated to approximately 0.1 mg/ml using molecular weight sieve filters (Vivascience) with molecular weight cutoffs of 50 kDa. Protein concentration was determined using the ADV01 protein concentration kit (Cytoskeleton, Inc.).

Fluorescent labeling: Cy3 and Cy2 were conjugated to the E422K scaffold and bR respectively using the Cy3/2 Ab Labeling Kit (Amersham Biosciences) and following the manufacturer's instructions. Dye:protein ratios were determined by comparing the absorbance of the protein at 280 nm and the absorbance of the CyDye at 670 nm and 532 nm respectively. In both cases, the ratios provided a 1:1 correlation, suggesting that a single CyDye molecule is present on each protein.

Native PAGE: Equal amounts of NLP samples (0.5-2 µg) are diluted with 2× native sample buffer (Invitrogen) and loaded onto 4-20% gradient pre-made Tris-HCl gels (Invitrogen). Samples are electrophoresed for 250 V·hrs at a constant 125V. After electrophoresis, gels are incubated with Sypro Ruby for 2 hours and then destained using 10% MeOH, 7% Acetic acid. Following a brief wash with ddH$_2$O, gels are imaged using a Typhoon 9410 (GE Healthcare) at 532 nm (green laser) with a 610 nm bandpass 30 filter. Molecular weights are determined by comparing migration vs. log molecular weight of standard proteins found in the NativeMark standard (Invitrogen). The Stokes diameter of the NLPs is calculated from the known Stokes diameter of the same proteins in the standard sample.

SDS PAGE: Protein fractions were analyzed by SDS-PAGE gels, stained with Sypro Ruby (BioRad) and fluorescently imaged with a Typhoon 9410 (GE Healthcare), as described above.

UV-visible spectroscopy: UV-visible spectra were collected using 50 uL of sample in a quartz cuvette on an ultrospec 5300pro UV/Visible spectrophotometer (Amersham Biosciences) Dark adapted spectra were collected after keeping the sample wrapped in foil overnight. Light adapted spectra were collected after exposure to a full spectrum bright light for 15 min. [Wang et al].

AFM imaging: Atomically flat Muscovite mica disks were glued to metal substrates to secure them to the scanner of a stand-alone MFP-3D AFM (Asylum Research, Santa Barbara, Calif.). 2 uL NLP solution at a 100 ng/mL concentration was incubated for two minutes on the mica surface in imaging buffer (10 mM MgCl$_2$, 10 mM Tris-HCL, and 0.1 M NaCl, adjusted to pH 8.0) then lightly rinsed through wicking. The AFM has a closed loop in the x, y, and z axes, which improved imaging fidelity. The topographical images were obtained with oxide sharpened silicon nitride levers (MSCT, Veeco, Santa Barbara, Calif.) with a spring constant of 0.1 N/m. Images were taken in alternate contact (AC) mode, also known as tapping mode, in aqueous environment, with amplitudes below 20 nm and an amplitude setpoint at 65% tapping amplitude scan rates were below 1.5 Hz. Height, amplitude, and phase images were recorded. Phase was monitored such that biphasic images were omitted. High resolution images of 600 nm by 600 nm were acquired at 512 by 512 pixel resolution, such that each NLP on average contained 600 pixels. The density of particles on the mica substrate was kept low, on average 90 particles per 1 um², to facilitate individual particle identification and sizing. Experiments were carried out in a temperature controlled room at 23+/−1° C., with acoustic hood isolation and active vibration damping.

AFM image analysis: Heights of features in images were examined by histogram analysis using Igor Pro Wavemetrics software routines, where contiguous particles were defined by a threshold height above the background and the height arbitrarily defined as the maximum height contained by 10 or more pixels within the particle.

Ion Mobility Spectrometry: IMS determines the mean aerodynamic diameter population distribution of particles in a volatile buffer. NLP samples were exchanged via dialysis into a 25 mM ammonium acetate buffer and the aerodynamic diameter of NLPs determined with a Macroion Mobility Spectrometer (Model 3890, TSI Inc., Shoreview, Minn.), as previously described (Bacher 2001). NLP aerodynamic diameters were subsequently converted to aerodynamic spherical volumes as previously described.

Example 1

Incorporation of Membrane Preparations from *Y. Pestis* in NLPs

Figure 3A:
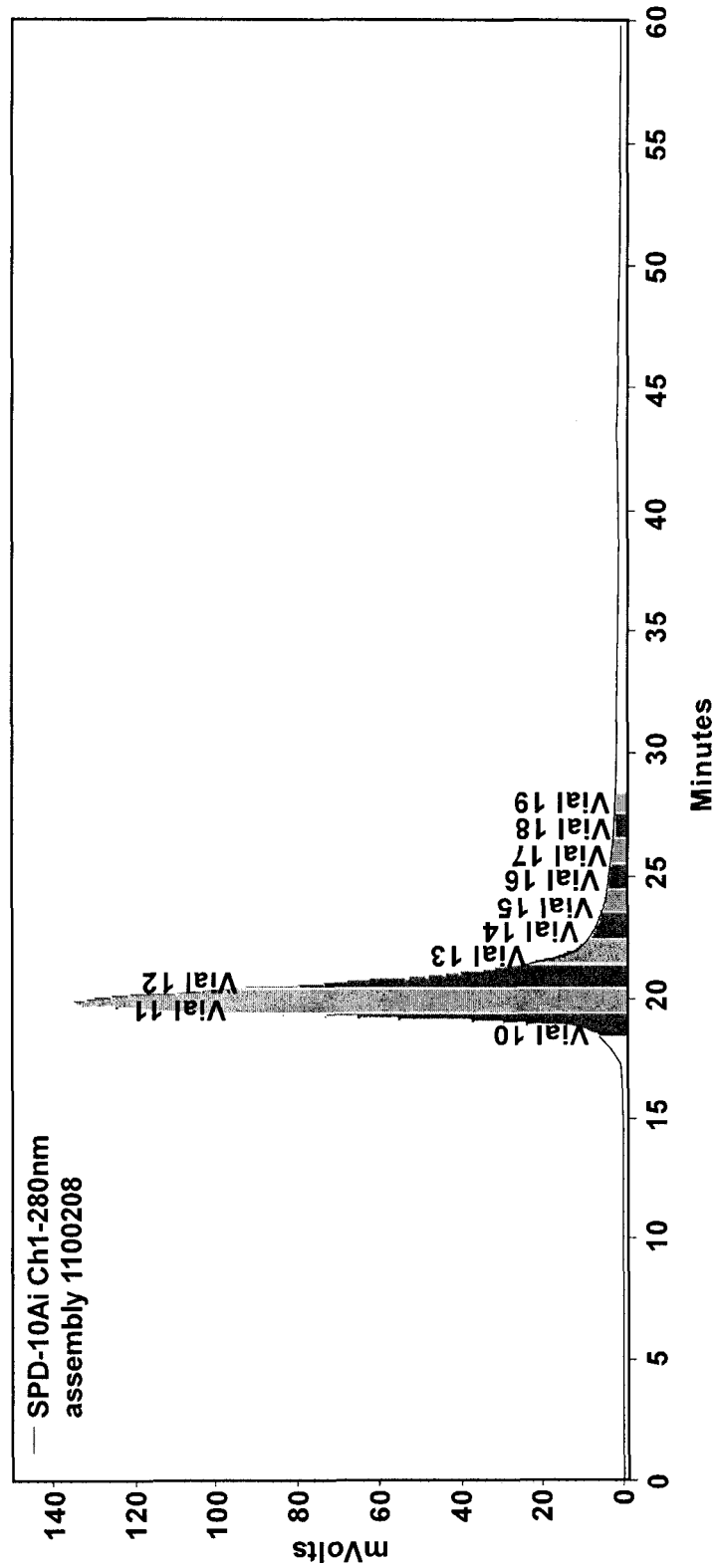
FIGS. 3A-3B show size exclusion chromatography (SEC) traces of 'empty' NLPs made using the in situ approach (as in FIG. 1) using two different ratios of lipid to scaffold protein.
Figure 3B:
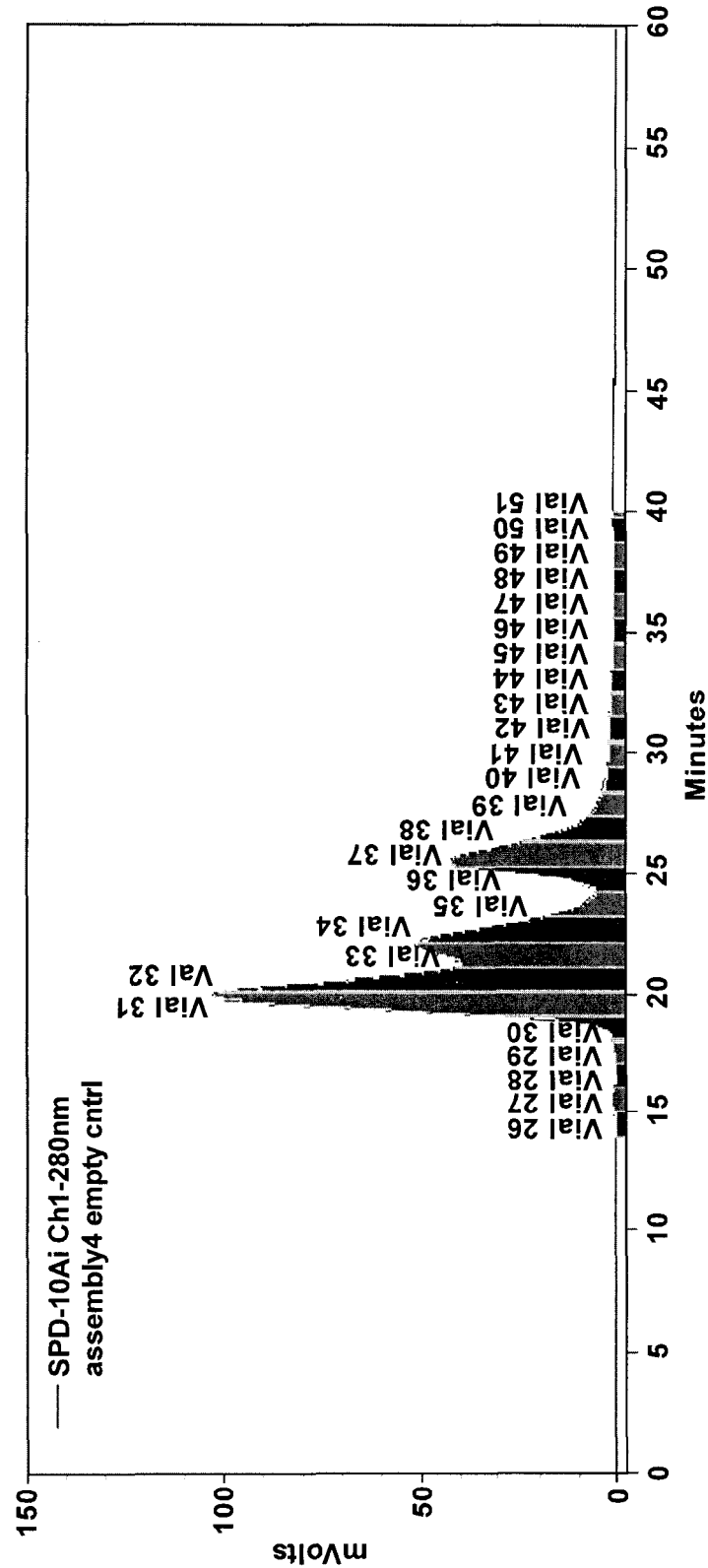
Figure 4E:
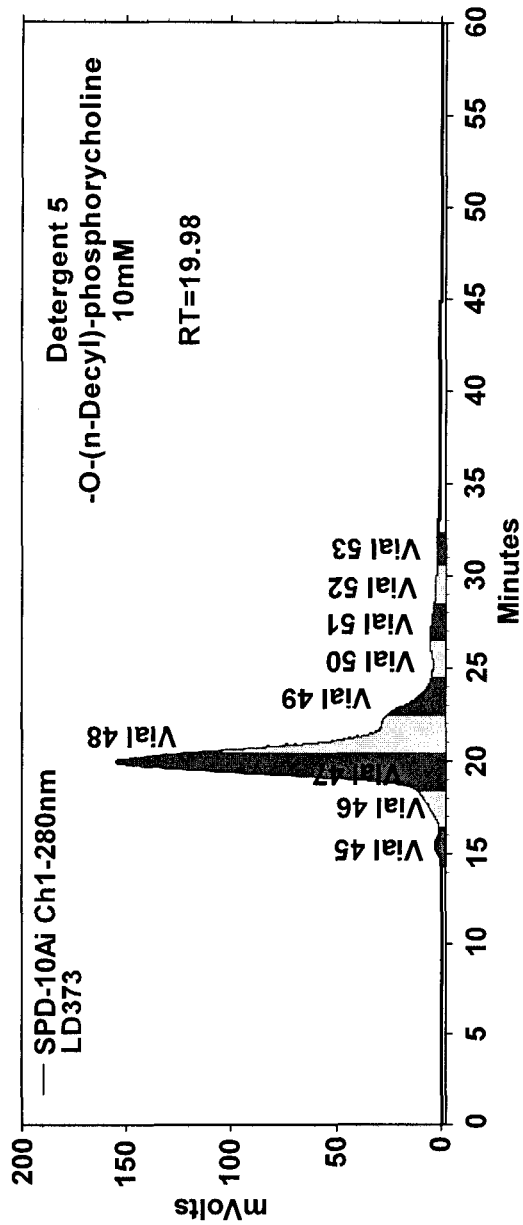
Figure 4F:
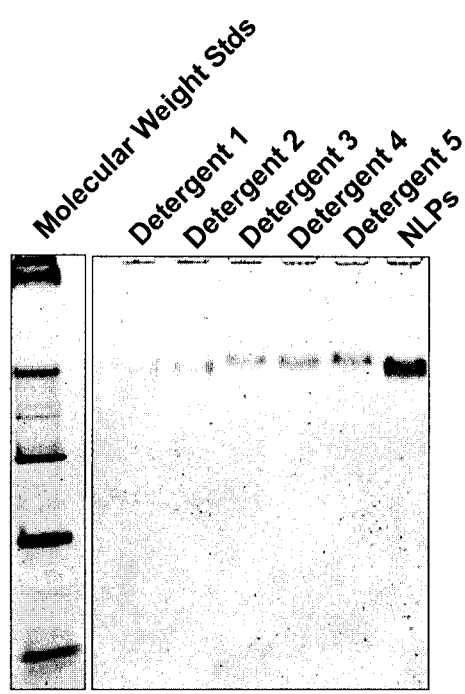

Membrane preparations from *Y pestis* are derived according to procedure herein illustrated. In those procedures, both wild-type and mutant strains can be used. FIGS. 3A and 3B show a native gel of MP-NLPs formed using the in situ method (FIG. 2) highlighting multiple sized NLP species. NLP bands are present at more than one location on the gel. These bands represent MP-NLPs of differing size and incorporate different sets of proteins from the membrane preparations. The size exclusion chromatography traces that gave rise to the different NLP bands are shown in FIGS. 4A-4E. As can be seen by comparing the species in NLP4v25 and NLP4v28 with the SEC trace in FIGS. 4A-4E, the molecular size of these MP-NLPs can be dramatically different. The membrane proteins that these differently sized MP-NLPs can accommodate are also different.

Gram-negative bacteria are grown in sufficient quantity to produce a large amount of membrane proteins (currently we grow 50-100 ml cultures). The bacteria are harvested and centrifuged (~1 k×g) to separate cells from growth media. Cells are lysed by a number of different methods: 1. sonication, 2. trituration in chemical lysis solutions, such as B-per from Pierce. 3. bead-beated with zirconium beads, 4 lysed using pressure in a French press or in the Pressure Biosystems Inc. PCT instrument. Mammalian and yeast cells can also be lysed by homogenization. Following lysis, samples are spun down and separated from nucleic acids, cell particles and other cell debris using a low speed centrifugation (16 k×g). Soluble proteins are then separated from membrane proteins using high speed centrifugation (100 k×g). Alternatively, membrane proteins can be incorporated into NLPs directly from cell lysates.

Example 2

Large NLP—Single Peak Optimization from Cholate Formed NLP

Membrane preparations from *Y pestis* are derived according to procedure herein illustrated. FIGS. 3A and 3B show the empty NLP that provides a single-sized NLP for eventual incorporation of membrane proteins. This method which varied the scaffold protein to lipid ratio to 1:6 on a mass ratio, highlights the ability to alter the NLP size to obtain the membrane proteins of interest.

Example 3

*Yersinia pestis* Outer Membrane Protein NLPs

Figure 15:
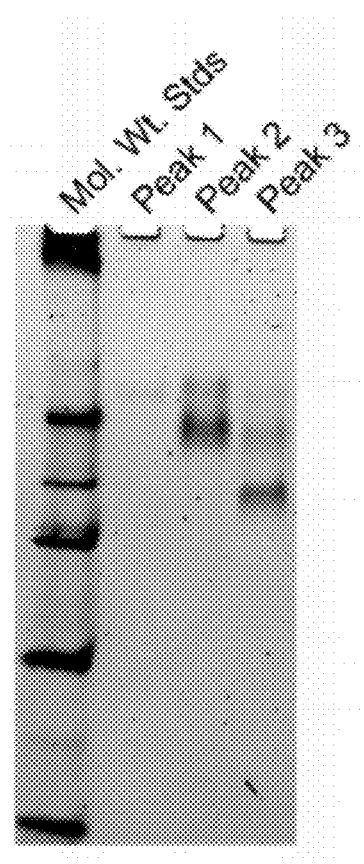
FIG. 15 shows a native gel of several different SEC fractions of MP-NLPs containing different molecular weights to specifically select different membrane proteins from the inner membrane of *Acinetobacter baumannii* at different ratios of membrane protein to scaffold protein. The different ratios (from 3:2 to 1:1) show no differences in assembly.
Figure 16:
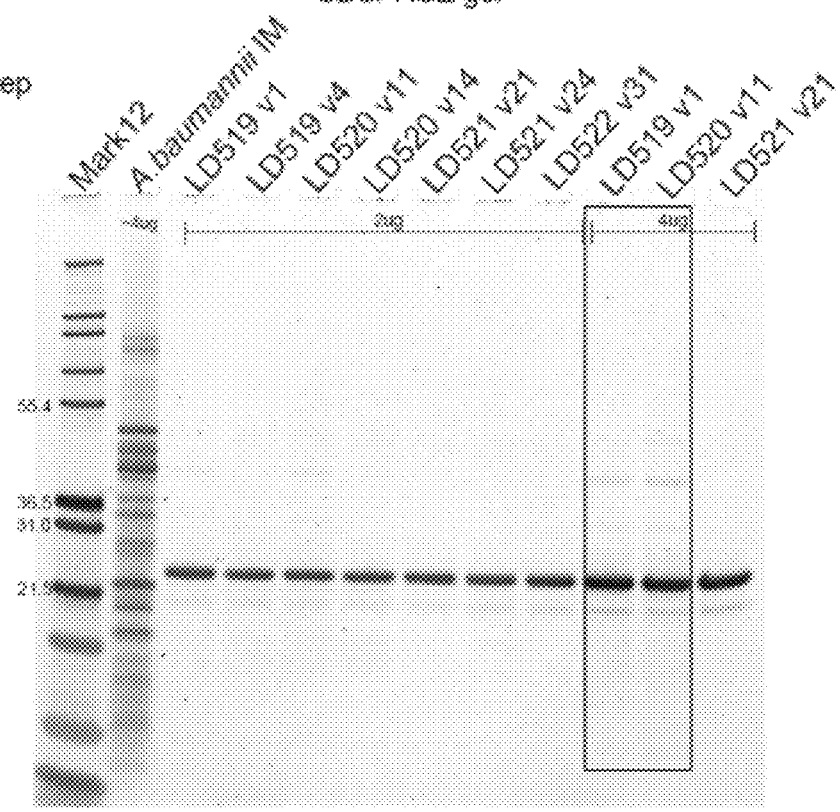
FIG. 16 shows the SDS-PAGE of incorporated *Acinetobacter baumannii* inner membrane proteins following in situ assembly of MP-NLPs using different ratios of scaffold protein to membrane protein (3:2 to 1:1). Multiple protein bands from this crude preparation are easily seen in the gel lane, showing that protein solubilization can be carried out using the methods herein for this membrane preparation.
Figure 17:
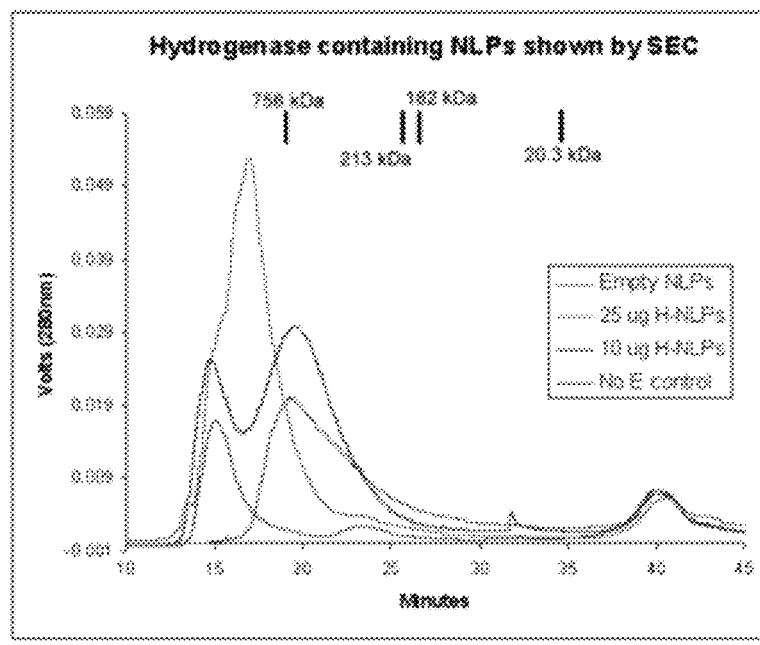
FIG. 17 shows an SEC trace overlay highlighting the molecular size differences between MP-NLPs, empty NLPs and crude membrane preparations. The SEC trace of Hydrogenase-NLPs is smaller than liposomes and larger than empty NLPs. This figure shows that different amounts of hydrogenase membranes (25 vs. 10 µg) can alter the pattern of incorporation. This data suggests a proper ratio of membrane protein to scaffold protein may be needed to have functional incorporation and that different ratios can be used to incorporate the membrane proteins of interest relative to the total set of membrane proteins in the complex.
Figure 19:
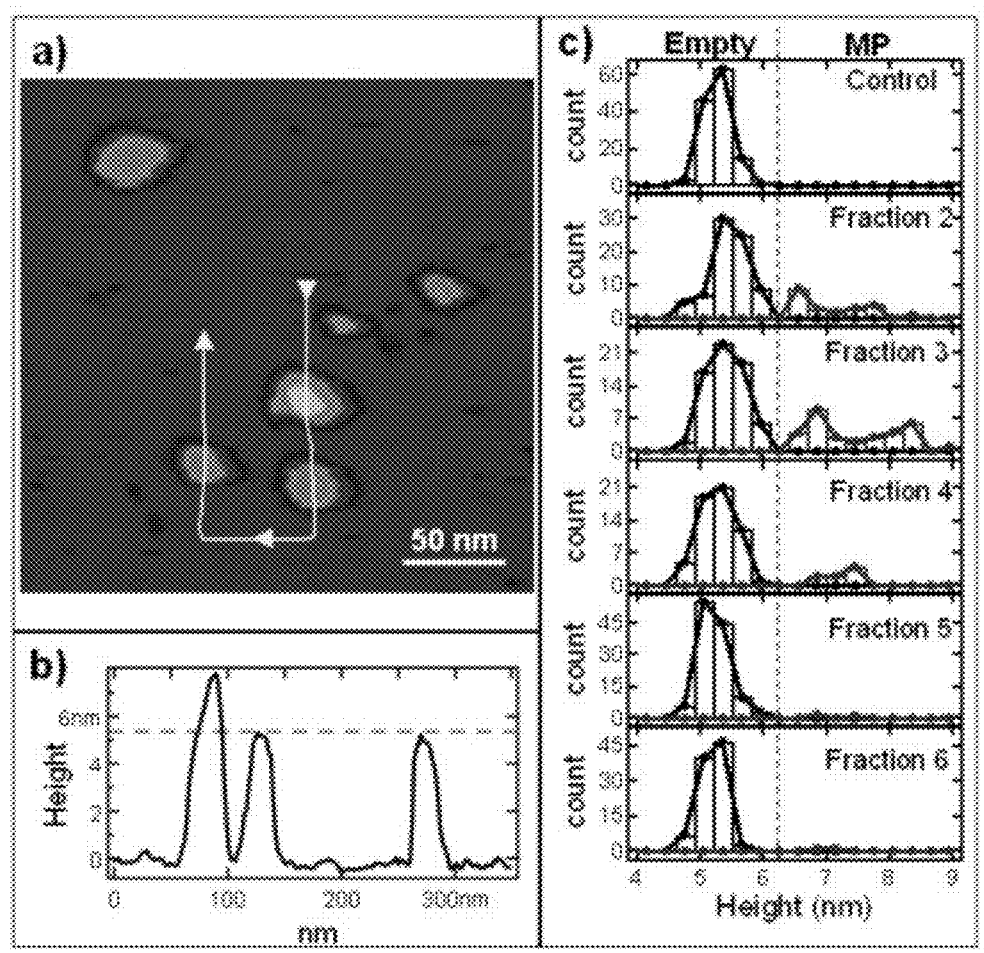
FIG. 19 shows AFM of hydrogenase incorporated NLPs. Panel A shows a top view AFM image of NLPs following SEC purification (fraction 3). Bright green regions are indicative of particles that are higher than 6.5 nm. Panel b shows a cross section of the three particles in A that have the arrow through them. Panel C shows histogram analysis of heights observed in NLPs that were formed without hydrogenase membrane fractions (so called 'empty' NLPs) and the different SEC fractions obtained following in situ formation of hydrogenase NLPs.
Figure 20:
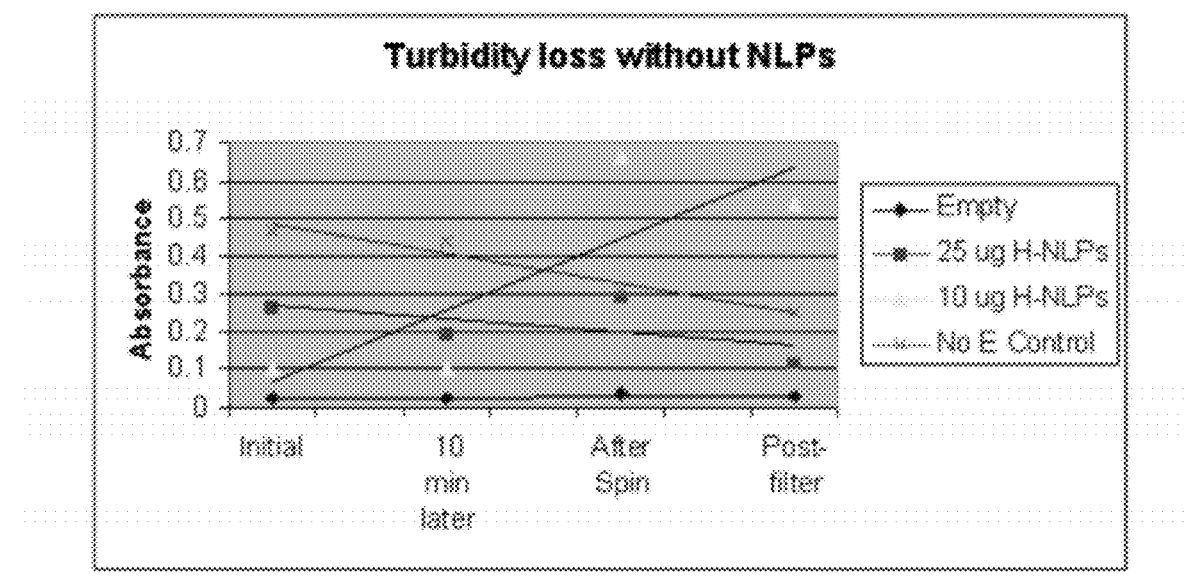
FIG. 20 shows a turbidity experiment that highlights the solubility of hydrogenase membrane proteins following in situ formation of MP-NLPs as opposed to the lack of solubility of the hydrogenase membrane proteins without NLP formation.
Figure 21:
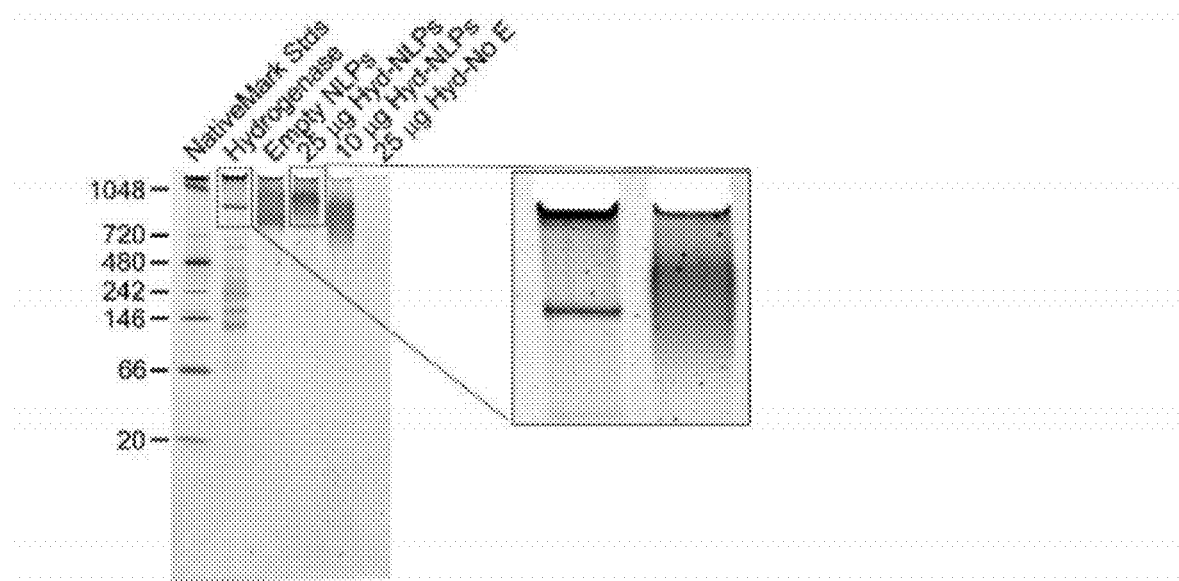
FIG. 21 shows native gel showing the molecular size of hydrogenase containing NLPs (MP-NLPs) and specifically highlights the reduced migration of the hydrogenase NLPs relative to 'empty' NLPs in the zoomed in part of the figure.
Figure 22:
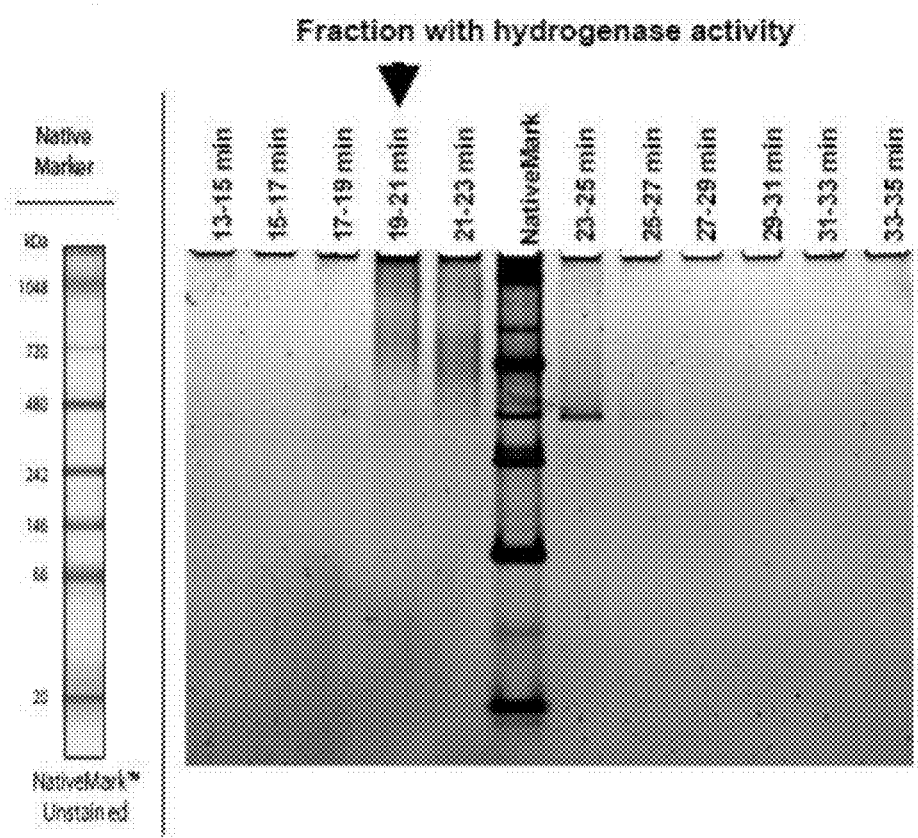
FIG. 22 shows a native gel showing the molecular size of MP-NLPs starting from hydrogenase membrane preparations. Native markers show relative molecular weight for the NLPs in the gel that correspond to different times of collection following SEC fractionation.
Figure 23:
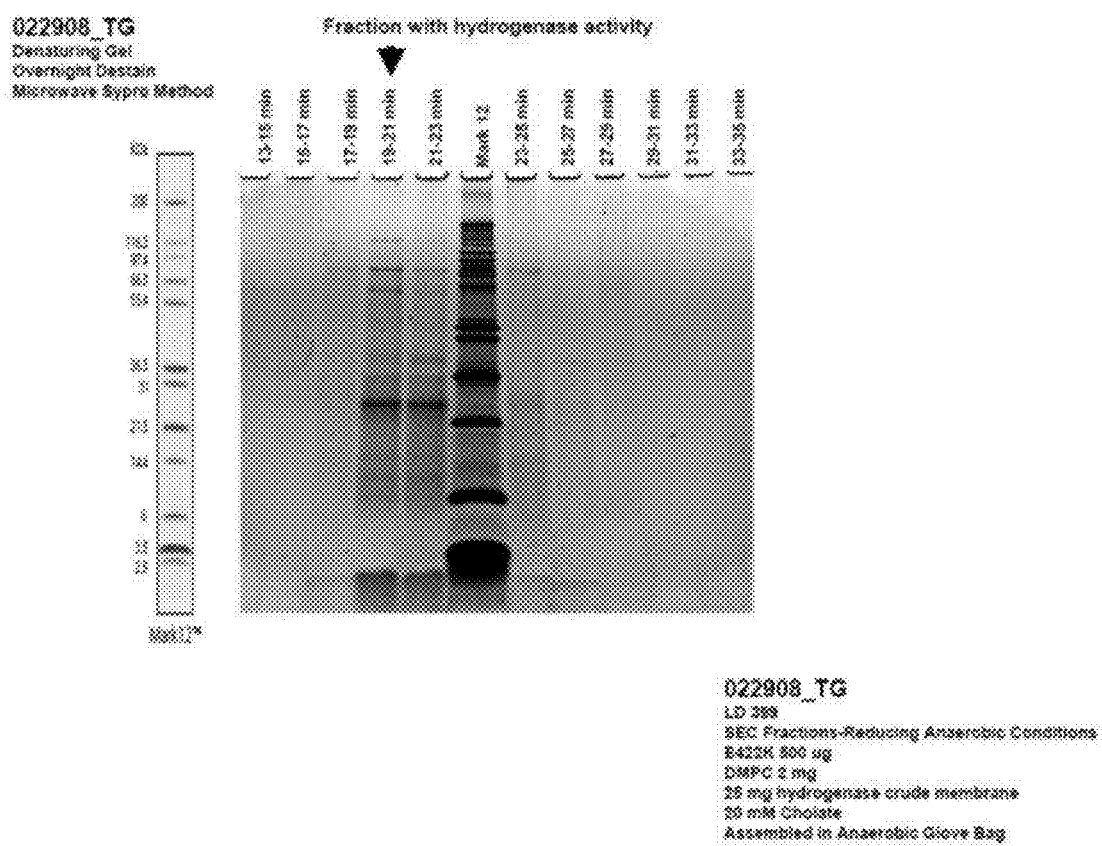
FIG. 23 shows the SDS-PAGE highlighting the different membrane proteins incorporated into hydrogenase NLPs based on the SEC fractionation profile.

Membrane preparations from *Y pestis*. In this embodiment, the MP-NLPs contain different NLPs based on the SEC fraction. For example, FIGS. 14-16 shows different *Y. pestis* outer membrane proteins are present in the different SEC fractions. SDS-PAGE highlights the particular protein bands that exist in the different fractions. The ratio of membrane protein to scaffold protein are 1.5:1 down to 1:1, showing similar results for these ratio levels.

Example 4

Virulence Factor AilC "Captured" Directly from *Y. pestis* Crude Membrane Fraction Direct capture of a membrane associated protein using the methods and systems of the present disclosure was performed using outer membrane (O.M.) fraction isolated from wild-type KIM D27 and AilC deletion mutant strains. In particular the OM fraction and the AilC mutant strain were used to assemble NLPs.

The cells were pelleted at 12 K×g and subsequently lysed with French Press. The membranes were centrifuged at 263 K×g and the outer membranes were separated from inner membranes by Triton X-100 solubilization and recentrifugation. E22K:AilC:OMPC (1:0.75:4) was then obtained in the presence of cholate (20 mM) in TSS.

Figure 8:
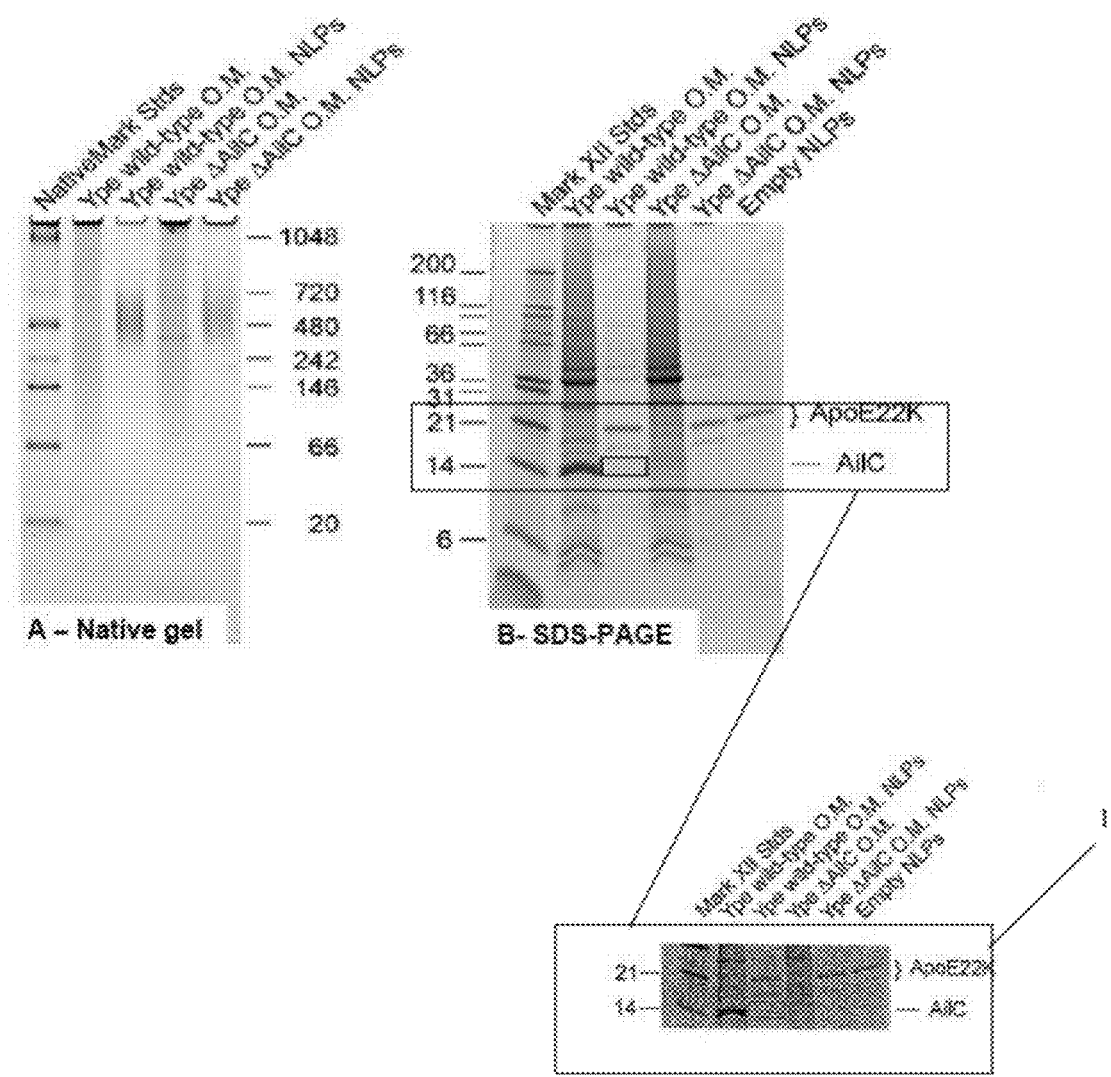
FIG. 8 shows a native gel and an SDS-PAGE gel of MP-NLPs that show the solubilization of AilC, a high abundant membrane protein from the *Y. pestis* outer membrane. Panel A shows a native gel that highlights the solubility of the MP-NLPS relative to the crude membrane fraction for both the wild-type strain that contains AilC and the knockout strain that does not contain AilC. Panel B shows the SDS-PAGE and highlights the captured, solubilized AilC in the black box. The zoomed in panel shows this more clearly.
Figure 9:
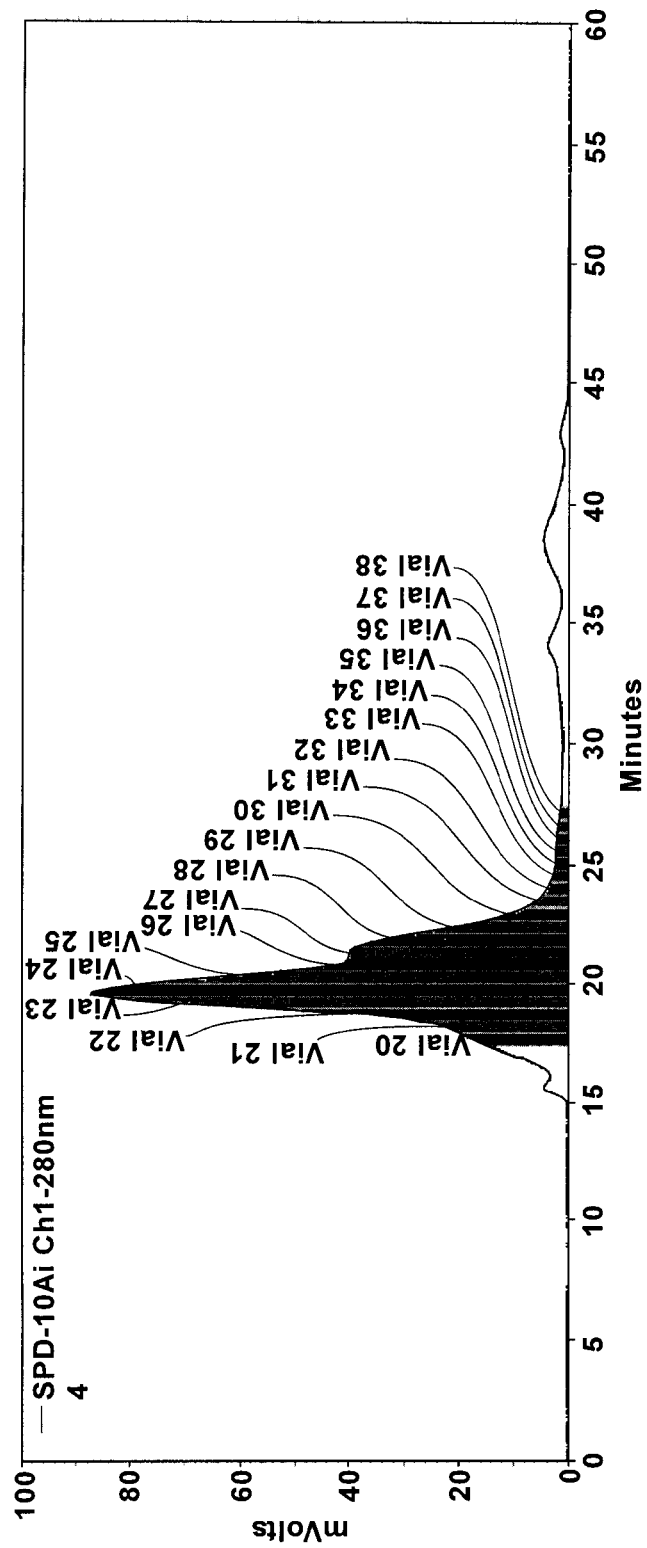
FIG. 9 shows an SEC trace of in situ formation using the optimized ratio of lipid to scaffold protein to obtain a single SEC peak that can be used to capture all of the membrane protein components as opposed to only the high abundant proteins.

The results illustrated in the SDS-PAGE of FIG. 8 indicate that the outer membranes from two different *Y. pestis* strains can be incorporated into NLPs. These results highlight the ability of this process to incorporate high abundant membrane proteins from particular membrane preparations. Importantly, the two strains differ only in the presence or absence of a particular high abundant outer membrane protein, called AilC. The AilC band on the SDS-PAGE is clearly evident in the highlighted box. The AilC knockout strain (ΔAilC) shows no AilC protein in the NLPs. All samples, empty NLPs, AilC knockout membrane-NLPs, and wild-type AilC-NLPs, all show the apoE422k apolipoprotein. The method used for these assemblies is shown in FIG. 1.

Example 5

Different Detergent Tested for the Formation of NLPs

Figure 5A:
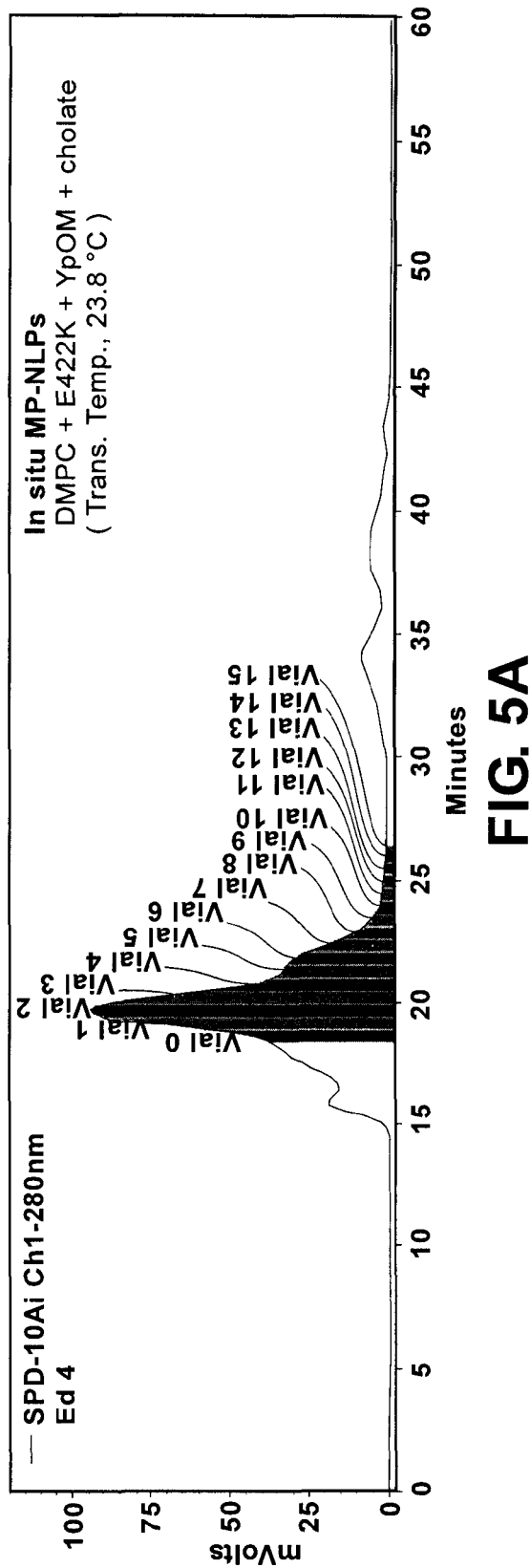
FIGS. 5A-5B show SEC traces of MP-NLPs using in situ formation as compared to the established detergent dialysis method. A higher yield of NLPs as determined by absorbance units in the MP-NLP fractions are obtained from the in situ method reported here (FIG. 5A) as compared to the detergent dialysis method (FIG. 5B).
Figure 5B:
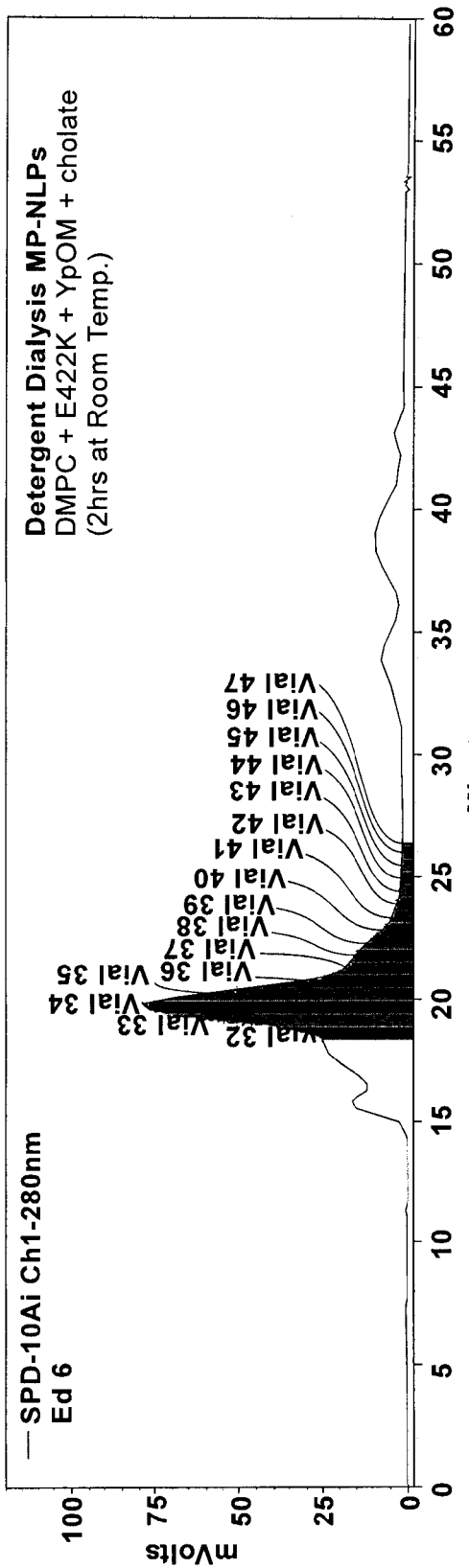
Figure 6:
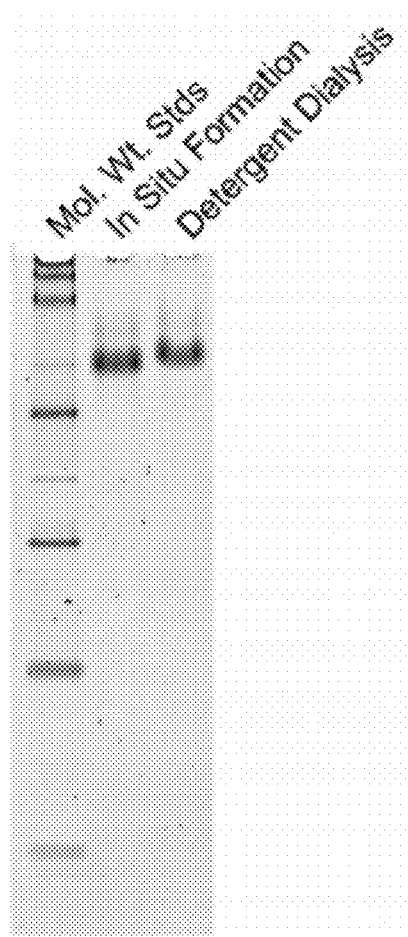
FIG. 6 shows a native gel highlighting the molecular weight and existence of NLPs in the in situ formation method as compared to the detergent dialysis method. Both preparations show a major band at ~700 kDa. These MP-NLPs show similar sized bands showing that the size and structure are consistent with nanolipoprotein particles.
Figure 7:
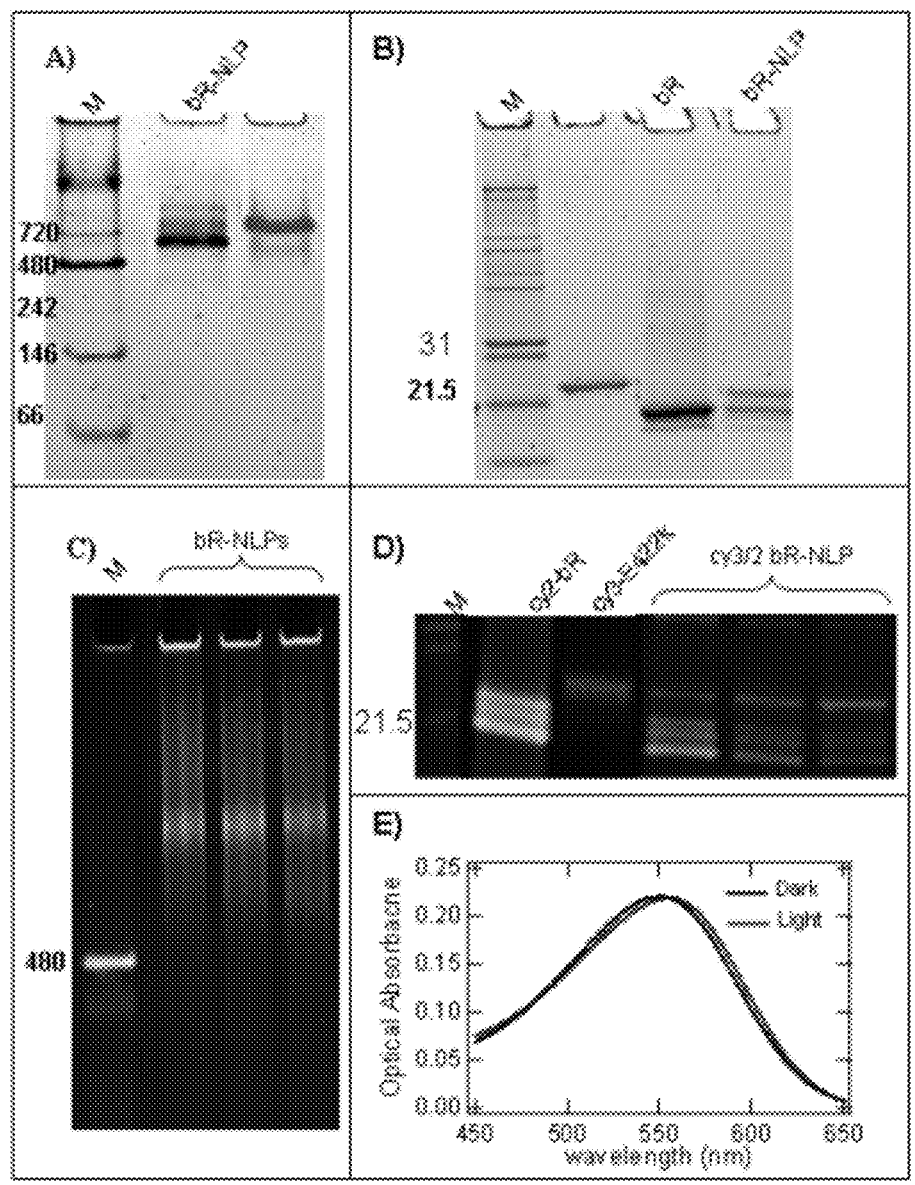
FIG. 7 shows MP-NLPs made using the in situ formation technique with a bacteriorhodopsin-containing purple membrane preparations obtained from the Haloarchaea, *Halobacterium salinarium*. Native gel, SDS PAGE and UV-visible spectroscopy of bR-NLPs. A) Native gel electrophoresis of bR-NLPs and empty-NLPs B) Tricine denaturing gel 16% SDS PAGE for an empty-NLP assembly, bR, and bR-NLP assembly. The bR-NLP lane displays two distinct bands corresponding to bR and apoE422k. C) Native gel electrophoresis of 3 SEC fractions spanning the entire NLP-rich peak for bR-NLPs assembled from cy2 labeled bR and cy3 labeled apoE422k, where green indicates cy2-E422k, red indicates cy3-bR and the yellow is the co-localization of both proteins D) Tricine denaturing gel 16% SDS PAGE of Cy2-bR, Cy3-apoE422k and 3 SEC fractions spanning the entire NLP-rich peak for bR-NLPs assembled from Cy2-bR and Cy3-apoE422k. The Cy3/Cy2 bR-NLPs contained two bands; a red band and green band indicating the presence of both cy2-bR and cy3-apoE422k. E) UV-Vis absorbance spectra showing 550.7 nm and 556.0 nm absorbance maxima for dark adapted bR-NLPs and light adapted bR NLPs respectively. Empty NLPs showed no significant absorbance at these wavelengths (not shown).
Figure 10:
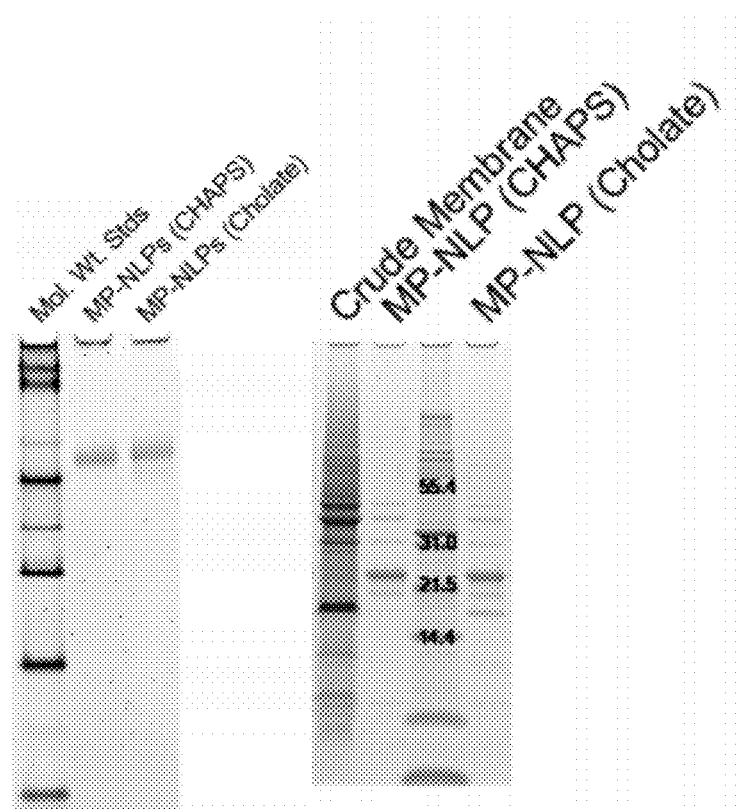
FIG. 10 shows a native gel (left) and an SDS-PAGE image (right) providing evidence that *Y. pestis* outer membrane proteins can be solubilized and incorporated into MP-NLPs. In particular, the membrane proteins incorporated in the MP-NLPs differ due to the detergent used (Cholate vs. CHAPS) and the ratio used.
Figure 11A:
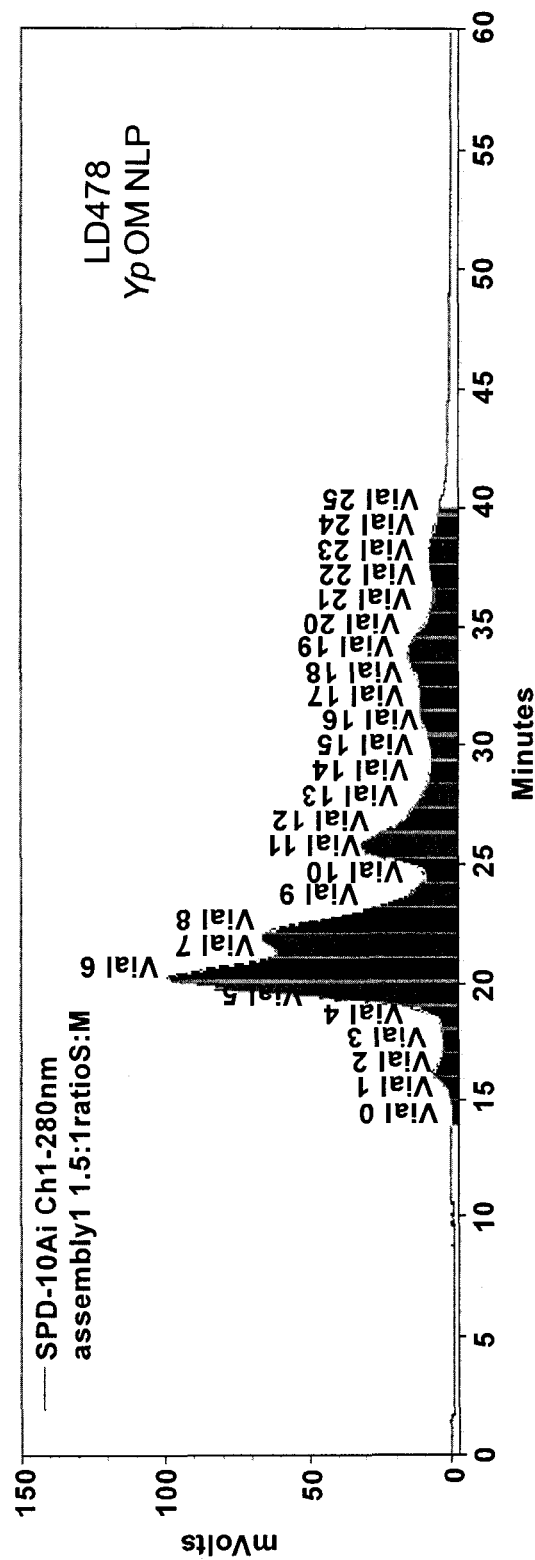
FIGS. 11A-11D show SEC traces of MP-NLPs using three different ratios of membrane protein to scaffold protein. No obvious differences are seen in yield for these different ratios, but the three peaks present in the SEC can be individually collected and these MP-NLPs contain different sized membrane components.
Figure 11B:
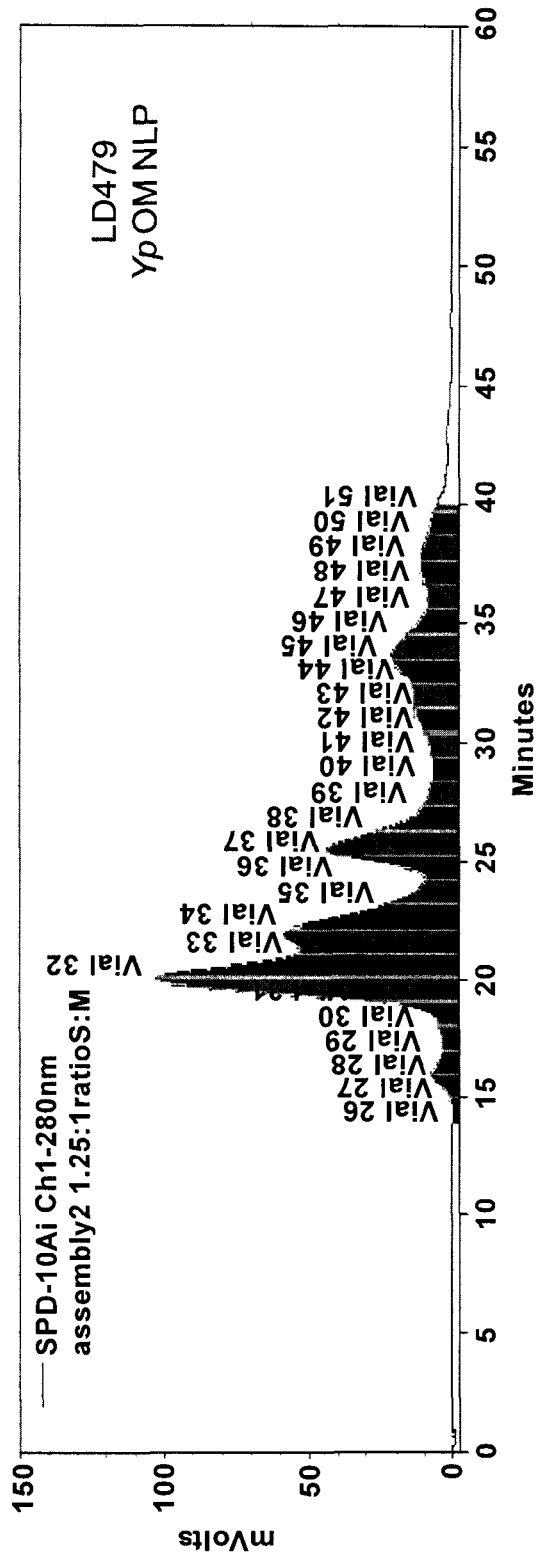
Figure 11C:
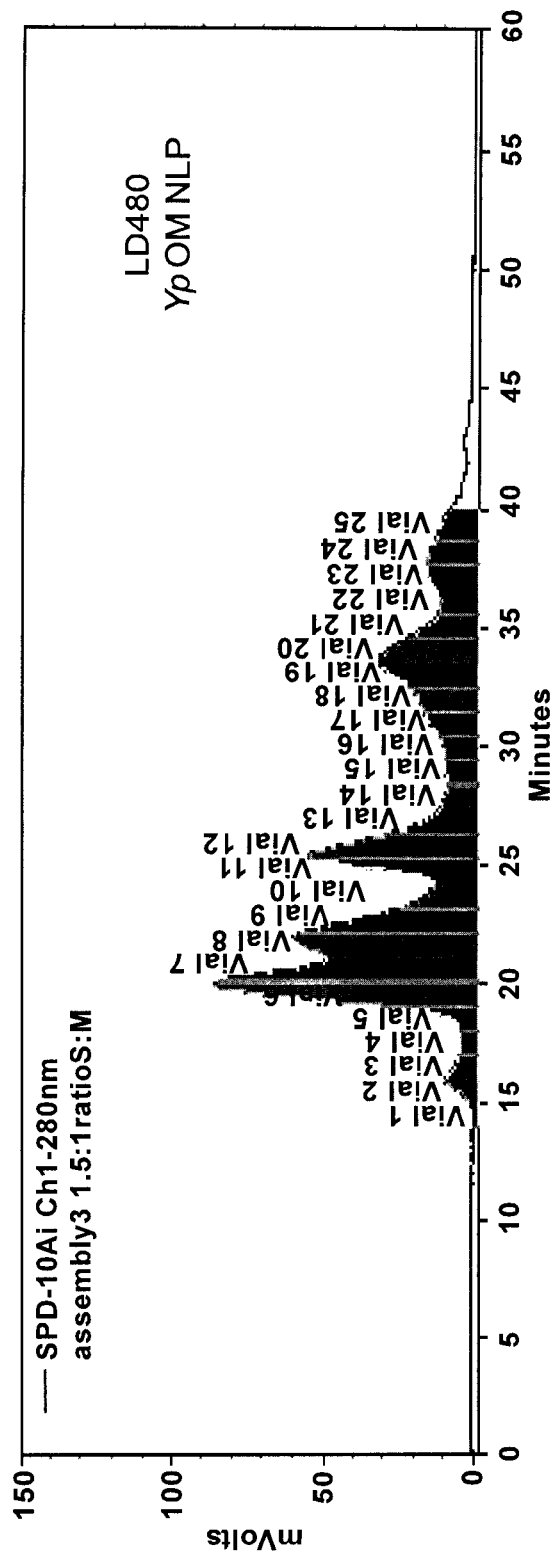
Figure 11D:
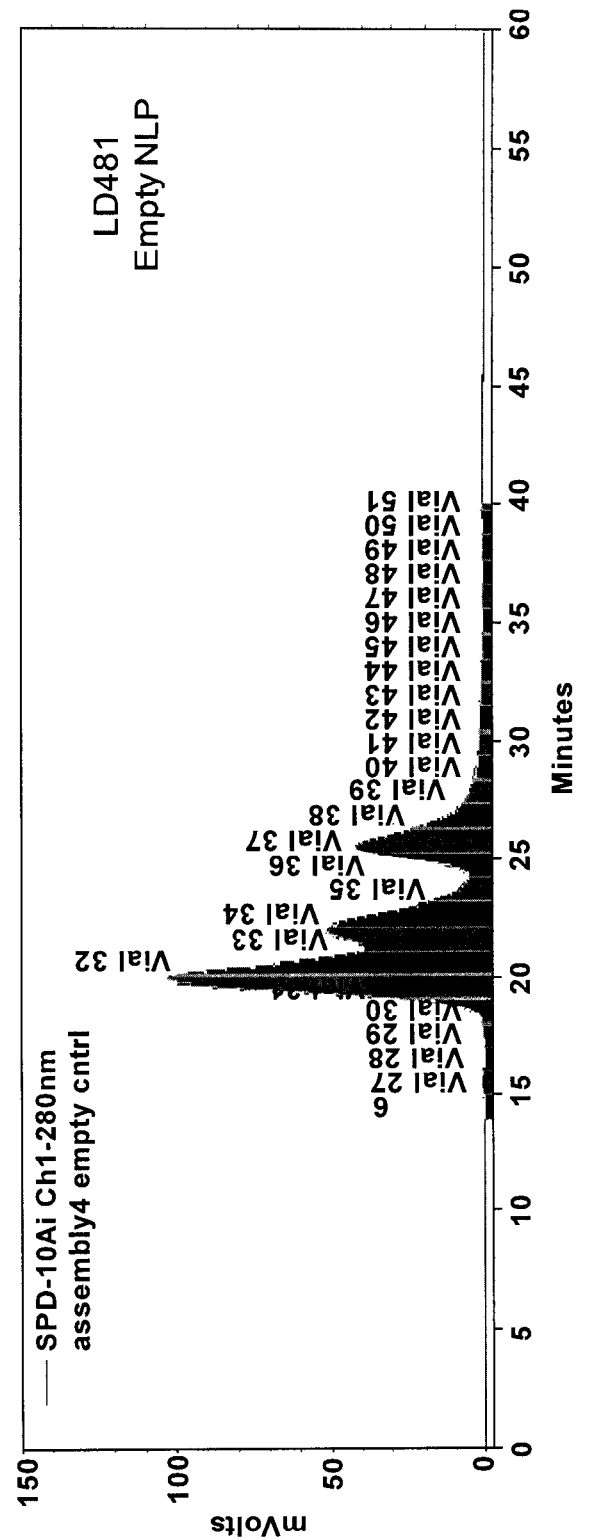
Figure 12:
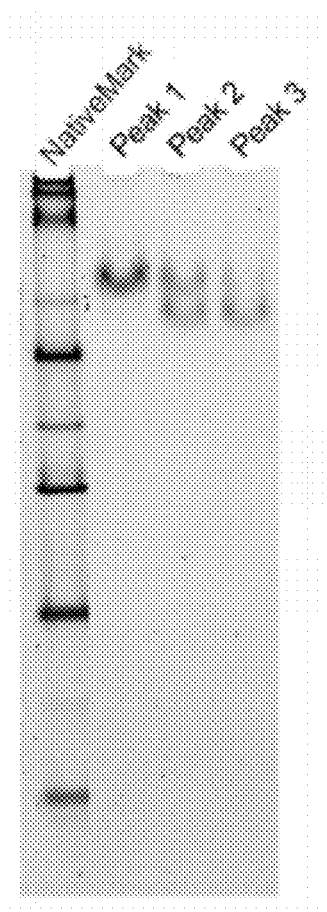
FIG. 12 shows a native gel showing the size (molecular weight) of different MP-NLPs. These MP-NLPs were made using the method shown in FIG. 1 and they comprise *Y. pestis* outer membrane preparations
Figure 13:
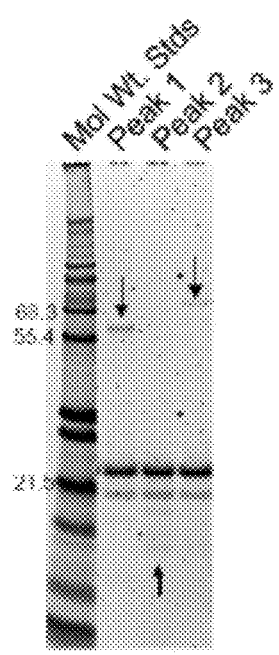
FIG. 13 shows an SDS-PAGE image highlighting the different *Y. pestis* outer membrane proteins that are incorporated into MP-NLPs of different size following SEC fractionation. The arrows denote two different high abundant *Y. pestis* proteins incorporated into two different NLP fractions.
Figure 14A:
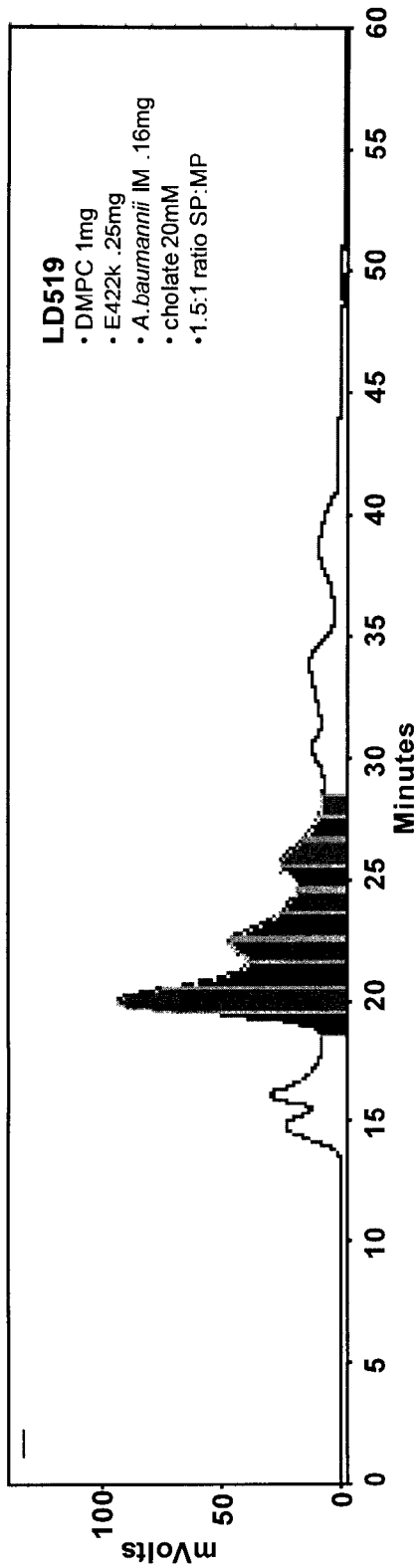
FIGS. 14A-14D show SEC traces of MP-NLPs using *Acinetobacter baumannii* inner membrane crude extracts. Multiple peaks in the SEC show the formation of different sizes of MP-NLPs that can be used to specifically incorporate different sets of membrane proteins from the crude extracts. Different ratios of scaffold protein to membrane protein are also effective.
Figure 14B:
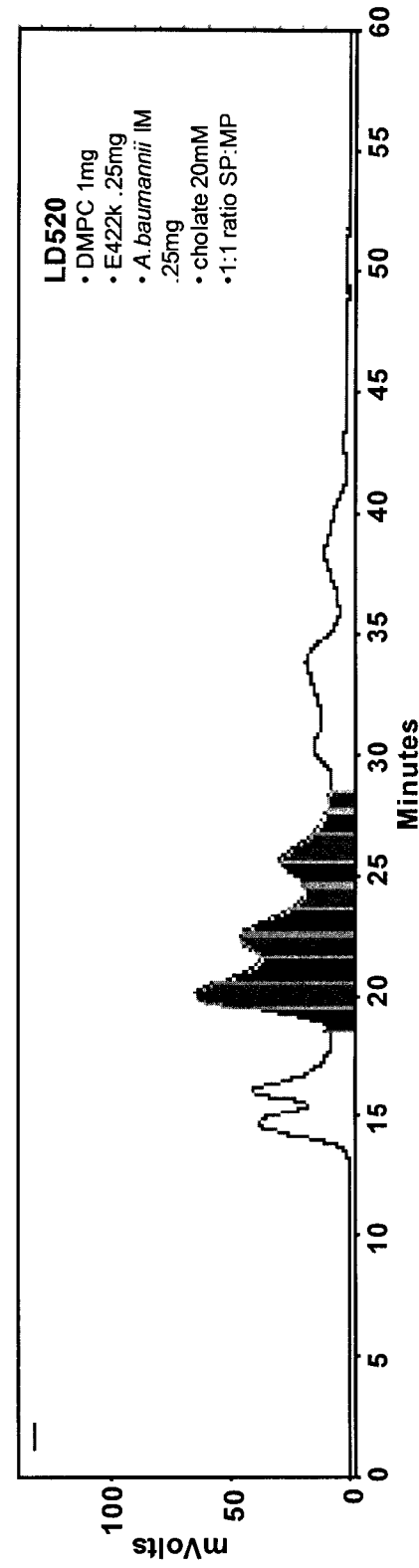
Figure 14C:
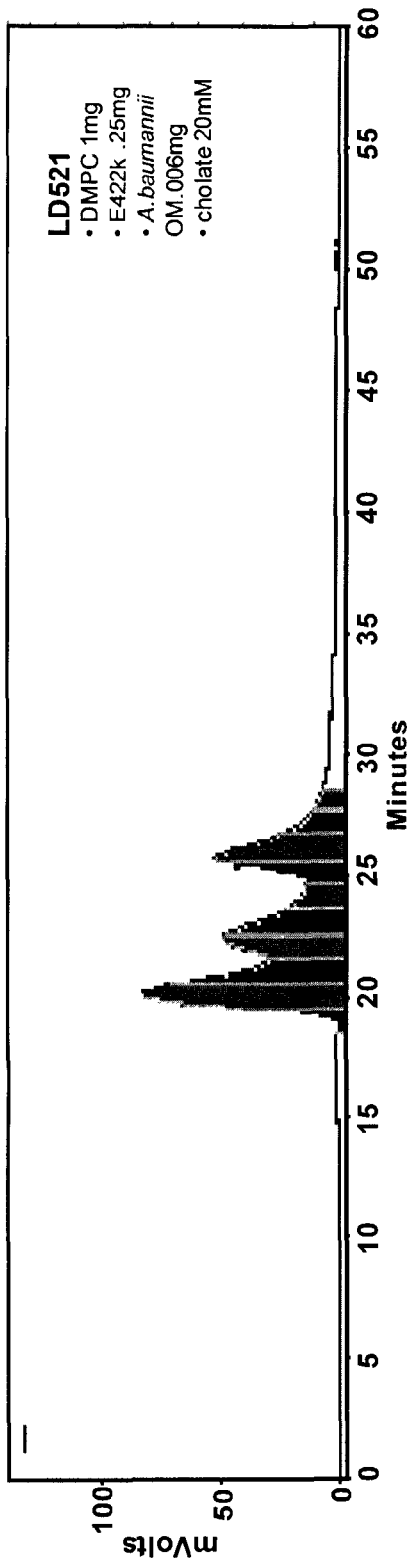
Figure 14D:
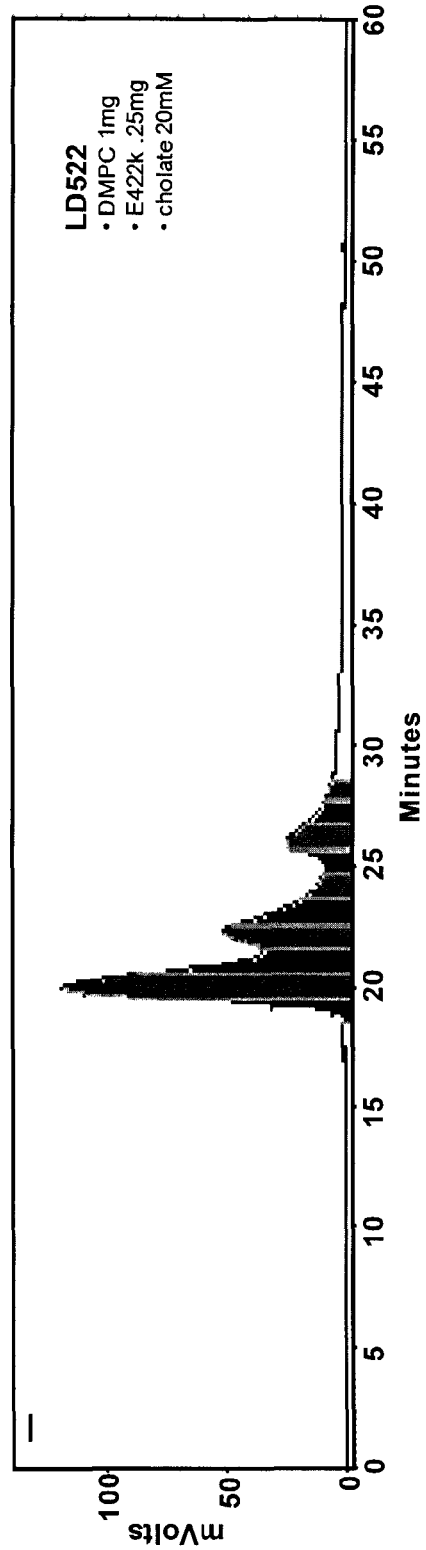

Membrane preparations from various sources can also be sequestered into NLPs using both methods shown in FIGS. 5 and 10 using detergents other than cholate. FIGS. 4A-4F show five different detergents that can be used to form NLPs. These include Pentaethylene glycol monodecylether, DDM, Chaps, Dimethlydodecylammonio propanesulfonate, and O-n-Decyl-phosphorylcholine. FIGS. 4A-4F show the SEC purified peak of NLPs and the native gel characterization showing the molecular weight and purity of the NLPs made with other detergents are all similar. FIGS. 4A-4F show the native page gel (panel A) and the SDS-PAGE (panel B) of *Y. pestis* membrane proteins incorporated into NLPs (MP-NLPs) using both CHAPs and cholate according to the methods established in FIG. 2.

Example 6

In Situ Vs. Detergent Dialysis

Figure 24:
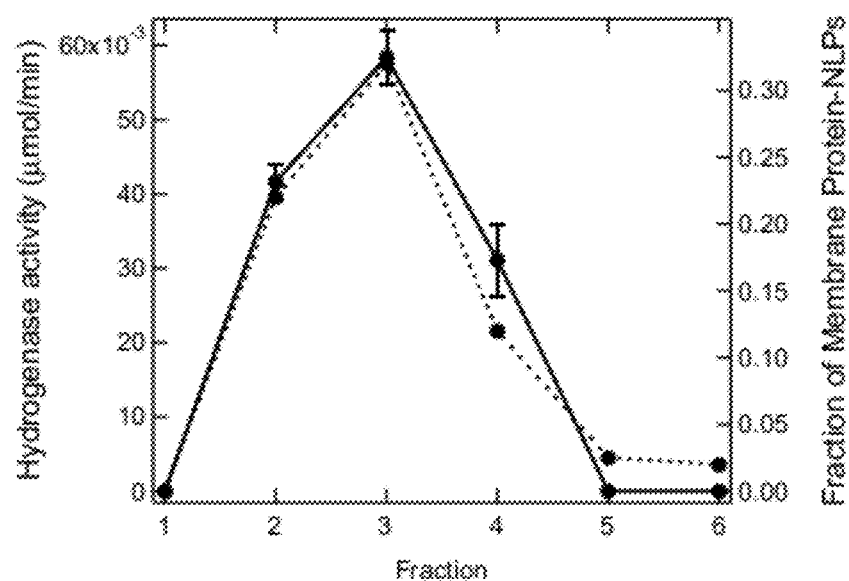
FIG. 24 shows hydrogenase activity as a function of NLP fraction. The activity (solid line) closely correlates with the fraction of NLPs that contain membrane protein (dotted line), as assessed by AFM. Fraction 3 had the highest level of hydrogenase activity and the highest percentage of membrane protein associated NLPs.
Figure 25:
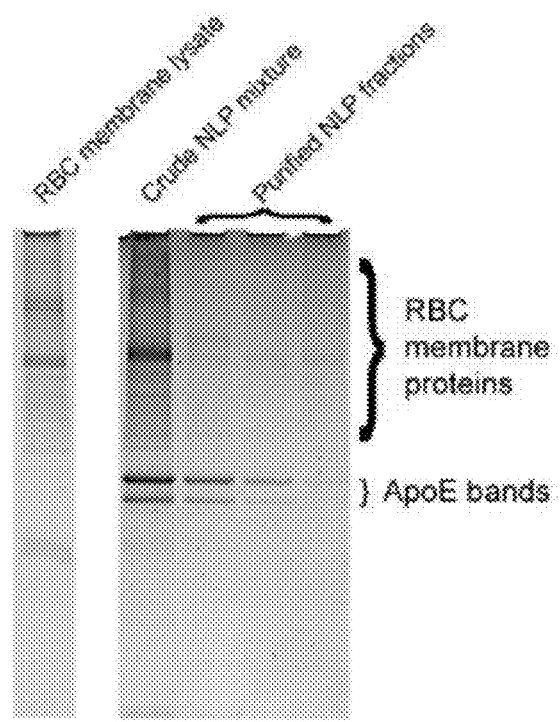
FIG. 25 shows an SDS-PAGE highlighting the major RBC membrane proteins incorporated into MP-NLPs. The RBC membrane lysate shows the crude membrane preparation that was used to obtain MP-NLPs using the in situ technique. The crude mixture shows the NLPs made following temperature transition, incubation, and detergent dialysis, but prior to SEC separation. The three lanes of purified NLP fractions show different levels of the high abundant RBC membrane proteins incorporated into the MP-NLPs.

Membrane preparations from *Y. pestis* were prepared using two different methods, namely in situ vs. detergent dialysis.

Example 7

Incorporation of Inner Membrane Preparations from *Acinetobacter Baumannii* in NLPs Membrane preparations from *A. Baumannii* were prepared using the inner membrane solubilization technique contained in this application, which is contained within the outer membrane technique. The results of incorporation are shown in FIGS. 20 to 23. FIG. 20 shows the size exclusion chromatography of multiple sized MP-NLPs using different ratios of membrane proteins relative to the apoE22k scaffold protein. The protocol followed was as shown in FIG. 2. FIG. 21 shows the membrane proteins that have been incorporated into NLPs by SDS-PAGE. Bands on the gel either correspond to the scaffold protein or to proteins that were solubilized from inner membranes into NLPs.

Example 8

NLPs Protein Capture of Hydrogenase from Crude Membrane Preparation

Proteins were captured in NLPs from crude membrane preparations according to an approach illustrated in the schematic representation of FIG. 1*b*.

In particular, total cell membranes were homogenized in 1 ml of homogenization buffer (10 mM Tris-HCl, pH 7.4, 1 mM EDTA, 200 mM sucrose, 1 mM phenylmethylsulfonyl fluoride, PMSF).—Nuclei and cell debris were removed from the homogenate by centrifugation at 900×g for 10 min at 4° C. The supernatant was centrifuged at 110,000×g for 75 min at 4° C. (SW40 rotor, Beckman ultracentrifuge) and the membrane pellet solubilized in buffer (10 mM Tris-HCl, pH 7.4, 1 mM EDTA, 0.5% Triton X-100, 1 mM PMSF) for a minimum of 1 h at 4° C. The insoluble material was then removed by centrifugation at 14,000×g for 10 min at 4° C. and 1 ug/ml aprotinin added to solubilized membrane samples prior to storage at 70° C.

The NLP so formed was used to analyze properties and functions of membrane proteins of interest. In particular, an in vitro H2 production from cellulosic Biomass and NLP-Hydrogenase membrane was performed according to the approach illustrated in the schematic representation of FIG. 1*b* following the teaching of Woodward et al (1996) Nature Biotech 14:872-876 herein incorporated by reference in its entirety.

Example 9

Monitoring Formation and Characterization of an NLP Particle Assembled using Methods and Systems Herein Disclosed Assembly of NLPs formed with the method and system illustrated in Example 2, was monitored using several techniques. In a first series of experiments, a specific fluorescent labeling was used to follow NLP formation according to an original approach illustrated in FIG. 7.

FIG. 7 shows the schematic of how fluorescently labeled MP-NLPs can be made. The technique is identical to the in situ formation shown in FIG. 2, except that fluorescent lipid and protein are implemented to better detect the formation of MP-NLPs. FIG. 7 shows the resulting MP-NLPs using the fluorescent tagged detection strategy by native and denatured gels. This figure also shows that in situ and ex situ techniques are both successful at assembling, solubilizing, and purifying membrane proteins from crude membrane preparations.

The inclusion and proper folding of a protein of interest into the NLP formed using the methods and systems herein disclosed was also verified by way of the methods and systems for monitoring production of a target protein in a nanolipoprotein particle described in U.S. patent application Ser. No. 12/118,530 herein incorporated by reference in its entirety.

Properly folded Bacterial Opsin (bOp) binds retinal (Ret) to give bacteriorhodopsin (bR) and turns purple. Both Invitrogen (IVGN) Expressway and Roche RTS reactions express active bOp in the presence of nanolipoprotein particles (NLPs) that binds Ret to produce functionally active bR.

Example 10

Characterization of Hydrogenase NLPs

Membrane preparations from *P. furiosus* were obtained as reported in to U.S. application entitled "Nanolipoprotein Particles comprising Functional Membrane Associated Biocatalysts and related Assemblies, Methods and Systems", filed on the same day of the present application.

Example 11

Solubilization of Hydrogenase Complex in NLPs

Membrane preparations from *P. furiosus* were incubated using the in situ formation technique and examined for turbidity (FIG. 20). The membranes that were not incubated with NLP components failed to stay in solution, instead quickly settling to the bottom of the tube. MP-NLP formation, however, maintained the hydrogenase membrane complex in solution, therefore, this technology was able to successfully solubilize the complex. FIG. 21 highlights the differences between the hydrogenase membranes that are insoluble and the membrane proteins that become soluble due to the in situ method.

Example 12

Hydrogenase Incorporated in NLPs Maintains Functionality

Membrane preparations from *P. furiosus* Cellular membranes from pfu lysates were separated from cellular debris and washed using centrifugation as previously described (Sapra 2000). A suspension of the membranes in TBS was added to a mixture of DMPC, apoE22k, and cholate (20 mM). The mixture was briefly vortexed and temperature cycled starting at 30° C. for ten minutes followed by 20° C. for ten minutes. This cycle was repeated two more times (3 times total). Following cycling, the mixture was incubated at 23.8° C. overnight. Following this overnight incubation at the transition temperature of DMPC, samples were separated by size exclusion chromatography to purify MP-NLPs from lipid-rich and lipid-poor structures. Fractions were then examined for structure by atomic force microscopy and tested for molecular weight and purity by native and SDS-PAGE. NLPs were tested for functional hydrogen production using and established gas chromatography assay (Sapra 2003). FIG. 24 shows the hydrogenase activity of the different NLP fractions. This result shows that the incorporated hydrogenase Example 13

Red Blood Cells (RBC) Membrane in NLPs

RBC membrane preparations were incorporated into NLPs and the more abundant RBC membrane proteins were successfully captured in NLPs. RBC membranes were made essentially as described (Pasini E M et al, 2006). Packed RBCs (10 mL) were suspended in 50 mL ice-cold 5 mM phosphate buffer, pH 8, and centrifuged (9000 g, 20 minutes, 4° C.). Hemolysate was discarded and the operation repeated (at least 5 times) until the supernatant appeared colorless. Centrifugation was then increased to 20 000 g and washing was repeated until the ghost membranes appeared yellow-whitish. Membranes were stored at −80° C. These crude RBC membranes were then added to apoE22k and DMPC in a ratio of (8:2:1) (DMPC:E422k:RBC membrane) in the presence of 20 mM cholate. The complex was vortexed, placed in temperature transition three times starting at 30° C. and then 20° C. Following transition, the sample was incubated o/n at the transition temperature of DMPC (23.8° C.).

Example 14

Solubilization of a Membrane Protein

Harvest total cell membranes from bacteria or other cells (yeast, mammalian cells, etc.) by high speed centrifugation (~100 k×g) following lysis and low speed centrifugation (~16 k×g). The lysis can be accomplished with sonication, rapid shaking with small glass or zirconium beads (bead beating), or chemical shearing. Pressure lysis can also generate appropriate lysis of cells to enable crude membrane capture. An example of this solubilization is shown in Blanchette et al., 2008.

Example 15

Purification of a Membrane Protein

In an exemplary procedure, starting from crude, or semi-purified cell membrane fractions, Applicants added them to a tube containing phospholipid (PL), purified apolipoprotein, a detergent surfactant, e.g. cholate in a solution of TBS. The mixture is subjected to a temperature cycle step based on the gel to liquid/crystalline transition temperature for the phospholipid and then incubated for 20-24 hours at the PL melting temperature (although shorter time for incubation may be sufficient). The detergent is then dialyzed out of the reaction mixture and the subsequent membrane protein containing NLP is separated from the unreacted PL and apolipoprotein by size-exclusion chromatography; the fractions containing NLPs are collected, pooled and concentrated by dialysis. For example, AilC was purified and solubilized from crude *Y. pestis* outer membrane fractions using DMPC, cholate, and apolipoproteinE422K yielding NLPs containing several proteins including the AilC target. Another example is to replace inner membrane proteins from *Acinetobacter baumannii* with everything else being the same The examples set forth above are provided to give those of ordinary skill in the art a complete disclosure and description of how to make and use the embodiments of the NLPs, methods and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of products, methods and system of the present disclosure, exemplary appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

References

1. Silvius, J. R. (1982) Thermotropic phase transitions of pure lipids in model membranes and their modification by membrane proteins. In Lipid-Protein Interactions (P. C. Jost and O. H. Griffith, Eds.) Vol. 2. New York: Wiley.
2. Cullis P R and Hope M J (1991) Physical properties and functional roles of lipids in membranes. In Biochemistry of Lipids, Lipoproteins, and Membranes (D. E. Vance and J. Vance, Eds.). Vol. 20. New York: Elsevier.
3. North P. and Fleischer S. (1983) *J. Biol. Chem.* Vol. 258, No. 2. pp. 1242-1253
4. Bockaert J., Brand C., Journot, L. (1997), Do Recombinant Receptor Assays Provide Affinity and Potency. In Receptor Classification: The integration of operational, structural, and transductional information (D. G. Trist, P. P. A. Humphrey, P. Leff, and N. P. Shankley, Eds.). Vol. 812. New York, N.Y. Academy of Sciences.
5. Tufteland M Peptides (2007) 28:741-748
6. Jonas, A. Methods Enzymol. 1986, 128, 553-82
7. Bayburt, T. H.; Grinkova, Y. V.; Sligar, S. G. Nano Lett. 2002, 2, 853-856
8. Chromy et al., 2007, Different Apolipoproteins Impact Nanolipoprotein Particle Formation. J. Amer Chem. Soc. 129, 14348-14354

9. J. Wang, S. Link, C. D. Heyes and M. A. El-Sayed, Comparison of the dynamics of the primary events of bacteriorhodopsin in its trimeric and monomeric states, Biophys. J. 83 (2002), pp. 1557-1566
10. G. Bacher, R. Korner, A. Atrih, S. J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of peptidoglycan fragments isolated from various *bacillus* species, J. Mass Spectrom. 36 (2001), pp. 124-139
11. Woodward et al (1996) Nature Biotech 14:872-876
12. Sapra R et al, J. Bacteriol. 2000 182, (12) 3423-3428.
13. Sapra R et al., J Bacteriol 2003, 100 (13), 7545-7550
14. Pasini E M et al., 2006 Blood, 108: 791-801
15. Blanchette et al., accepted (BBA membranes) Biochem Biophys Acta. 2008, Dec. 8. [Epub ahead of print] Atomic force microscopy differentiates discrete size distributions between membrane protein containing and empty nanolipoprotein particles.

What is claimed is:

1. A method for assembling a membrane associated protein, a scaffold protein, and a membrane forming lipid into a nanolipoprotein particle, the membrane forming lipid having a membrane forming lipid gel-crystalline transition temperature, the method comprising
    contacting the membrane associated protein with the scaffold protein and the membrane forming lipid to provide an admixture; and
    subjecting the admixture to multiple temperature transition cycles in presence of a detergent, for a time and under condition to allow assembly of the nanolipoprotein particle, the temperature transition cycle comprising:
    a temperature increase step wherein the admixture is brought to a temperature above said membrane forming lipid gel crystalline transition temperature and
    a temperature decrease step wherein the admixture is brought to a temperature below said membrane forming lipid gel crystalline transition temperature.

2. The method of claim 1, wherein the membrane forming lipid is contacted with the membrane associated protein and the scaffold protein at a temperature above the membrane forming lipid gel-crystalline transition temperature.

3. The method of claim 1, wherein the temperature increase step and/or the temperature decrease step are performed for a time and under conditions such that at least a fraction of the membrane forming lipid molecules in the admixture changes state.

4. The method of claim 1, wherein the membrane associated protein contacted with the membrane forming lipid and with the scaffold protein is comprised in a cell membrane.

5. The method of claim 1, further comprising incubating the admixture subjected to the temperature transition cycle at the membrane forming lipid gel-crystalline transition temperature for a predetermined amount of time that is functional to a desired amount of assembled nanolipoprotein particles.

6. The method of claim 1, further comprising removing the detergent from the admixture subjected to the temperature transition cycle.

* * * * *